US008710265B2

(12) United States Patent
Jessop et al.

(10) Patent No.: US 8,710,265 B2
(45) Date of Patent: Apr. 29, 2014

(54) SWITCHABLE SOLVENTS AND METHODS OF USE THEREOF

(71) Applicants: Georgia Tech Research Corporation, Atlanta, GA (US); Queen's University at Kingston, Kingston (CA)

(72) Inventors: Philip G. Jessop, Kingston (CA); Charles A. Eckert, Atlanta, GA (US); Charles L. Liotta, Atlanta, GA (US); David J. Heldebrant, Richland, WA (US)

(73) Assignees: Queen's University at Kingston (CA); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/969,984

(22) Filed: Aug. 19, 2013

(65) Prior Publication Data

US 2013/0327989 A1    Dec. 12, 2013

Related U.S. Application Data

(60) Continuation of application No. 13/172,090, filed on Jun. 29, 2011, now Pat. No. 8,513,464, which is a division of application No. 11/717,172, filed on Mar. 13, 2007, now Pat. No. 7,982,069.

(60) Provisional application No. 60/781,336, filed on Mar. 13, 2006.

(51) Int. Cl.
*C07C 257/00*    (2006.01)

(52) U.S. Cl.
USPC ........................... 564/245; 564/225; 564/244

(58) Field of Classification Search
None
See application file for complete search history.

(56) References Cited

U.S. PATENT DOCUMENTS

| | | | | |
|---|---|---|---|---|
| 5,457,083 | A * | 10/1995 | Muia et al. | 504/128 |
| 5,905,061 | A * | 5/1999 | Patel | 507/129 |
| 6,218,342 | B1 * | 4/2001 | Patel | 507/129 |
| 6,499,546 | B1 * | 12/2002 | Freeman et al. | 175/66 |
| 7,982,069 | B2 * | 7/2011 | Jessop et al. | 564/238 |
| 8,283,385 | B2 * | 10/2012 | Jessop | 516/22 |
| 8,513,464 | B2 * | 8/2013 | Jessop et al. | 564/245 |

* cited by examiner

*Primary Examiner* — Sudhakar Katakam
(74) *Attorney, Agent, or Firm* — Angela Lyon

(57) ABSTRACT

A solvent that reversibly converts from a nonionic liquid mixture to an ionic liquid upon contact with a selected trigger, e.g., contact with $CO_2$, is described. In preferred embodiments, the ionic solvent is readily converted back to the nonionic liquid mixture. The nonionic liquid mixture includes an amidine or guanidine or both, and water, alcohol, or a combination thereof. Single component amine solvents that reversibly convert between ionic and non-ionic states are also described. Some embodiments require increased pressure to convert; others convert at 1 atmosphere.

53 Claims, 14 Drawing Sheets

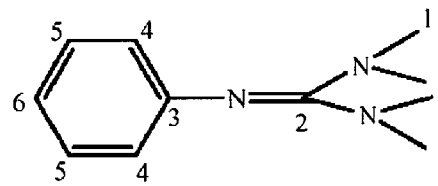

¹H NMR chemical shifts of N,N,N',N'-tetramethyl-N"-phenylguanidine, its bicarbonate salt and HCl salt in CDCl₃[a]

| Compound | H1 | H4 | H5 | H6 |
|---|---|---|---|---|
| tetramethylphenylguanidine | 2.7 | 6.7 | 7.2 | 6.8 ppm |
| tetramethylphenylguanidinium bicarbonate salt | 3.0 | 7.1 | 7.4 | 7.2 |
| tetramethylphenylguanidinium hydrochloride salt | 3.0 | 7.1 | 7.5 | 7.2 |

[a] $H_1$ appears as a singlet, $H_4$ as doublet and $H_5$ and $H_6$ as triplets.

¹³C NMR chemical shifts (in ppm) of N,N,N',N'-tetramethyl-N"-phenylguanidine, its bicarbonate salt and HCl salt in CDCl₃

| Compound Name | $C_1$ | $C_2$ | $C_3$ | $C_4$ | $C_5$ | $C_6$ |
|---|---|---|---|---|---|---|
| tetramethylphenylguanidine | 39.8 | 162.7 | 152.2 | 121.4 | 130 | 122.3 |
| tetramethylphenylguanidinium bicarbonate salt | 39.9 | 159.5 | 138.8 | 121.3 | 130.3 | 125.7 |
| tetramethylphenylguanidinium hydrochloride salt | 40.8 | 160.5 | 139.8 | 122.7 | 131.8 | 127.3 |

Figure 7

SWITCHABLE SOLVENTS AND METHODS OF USE THEREOF

CROSS-REFERENCE TO RELATED APPLICATIONS

This application is a continuation of application Ser. No. 13/172,090 filed Jun. 29, 2011, now U.S. Pat. No. 8,513,464, which is a continuation of application Ser. No. 11/717,172 filed Mar. 13, 2007, now U.S. Pat. No. 7,982,069, which claims the benefit under 35 U.S.C. s.119(e) of provisional patent application Ser. No. 60/781,336 filed Mar. 13, 2006, the contents of all of which are hereby incorporated by reference in their entirety.

STATEMENT REGARDING FEDERALLY-SPONSORED RESEARCH AND DEVELOPMENT

This invention was made with Government support under DE-FG02-99ER14986 contract awarded by the United States Department of Energy. The Government has certain rights in the invention.

FIELD OF THE INVENTION

The field of the invention is solvents, and specifically solvents that can be reversibly converted between ionic and nonionic forms.

BACKGROUND OF THE INVENTION

Conventional solvents have fixed physical properties which can lead to significant limitations in their use as media for reactions and separations. Many chemical production processes involve multiple steps such as reaction, separation, extraction and/or dissolution, and often the type of solvent that is optimal for any one step is different from that which is optimal for the next step. Thus it is common for the solvent to be removed after each step and a new solvent added in preparation for the next step. This removal and replacement greatly adds to the economic cost and environmental impact of such processes. Therefore, there exists a need for a solvent that can change Its physical properties.

Solvents are commonly used to dissolve material in manufacturing, cleaning, dyeing, extracting, and other processes. In order for a solvent to dissolve a material quickly, selectively, and in sufficient quantity, it is usually necessary for the solvent to have particular physical properties. Examples of such properties include dielectric constant, polarizability, acidity, basicity, viscosity, volatility, hydrogen-bond donating ability, hydrogen-bond accepting ability and polarity. At some point in such a process after the dissolution, separation of the material from the solvent may be desired. Such a separation can be expensive to achieve, especially if the solvent is nonvolatile as is commonly the case for polar solvents.

Moderate changes in temperature and pressure cannot be used as a method for dramatically changing solvent properties as they cause only minor changes in a conventional solvent's physical properties. Some high-pressure fluids can be continuously and reversibly changed by variations in pressure. Examples include supercritical fluids such as $CHF_3$ (Jessop, 1999), and $CO_2$-expanded liquids such as subcritical mixtures of $CO_2$ and organic liquid (Subramaniam, 2002). A disadvantage of such fluids or liquids is the pressure required (greater than 25 bar and often greater than 50 bar) causes added expense, inconvenience and risk.

There is a need for liquids that are able to switch by application of a trigger from one form with a first set of physical properties to another form with a second and different set of physical properties.

SUMMARY OF THE INVENTION

In a first broad aspect, the invention provides switchable solvents and methods of preparing and using such solvents. The solvents are based on amidine or guanidine and switch between a neutral form and a charged form (amidinium or guanidinium) in response to selected trigger. When prepared as described hereinbelow, the charged form provides an ionic liquid below 100° C., e.g., at room temperature. The trigger to change from neutral form to charged form may be exposure of the neutral form to $CO_2$, $CS_2$, or COS. Given its convenience, $CO_2$ is especially preferred. In preferred embodiments, solvents of the invention are not only switchable, but reversibly so, and removal of the trigger, e.g., removing $CO_2$, causes the charged form to switch to the neutral form.

In a second broad aspect, the invention provides switchable solvents and methods, of preparing and using such solvents, where the solvents are based on amidine or guanidine and switch between a first form with no local charges and a second, zwitterionic form in response to selected trigger. The trigger to change from first form to second, zwitterionic form may be exposure of the first form to $CO_2$, $CS_2$, or COS. Given its convenience, $CO_2$ is especially preferred. Preferably, a solvent according to this aspect of the invention is not only switchable, but reversibly so, and removal of the trigger, e.g., removing $CO_2$, causes the second, zwitterionic form to switch to the first form.

It should be understood that it is appropriate for purposes of the present disclosure to call removal of a first trigger a "trigger" itself, in that it causes a change in properties of the compound in question.

An aspect of the invention is a solvent that is an ionic liquid whose ionic character is changed such that it becomes a nonionic liquid in response to a trigger. Another aspect of the invention is a solvent that is a nonionic liquid whose nonionic character is changed such that it becomes an ionic liquid in response to a trigger.

According to a further aspect, the invention provides an ionic liquid that is formed by the reversible reaction of carbon dioxide with an amidine or guanidine and water. Reversibility has been observed as described hereinbelow for both amidine and guanidine.

In one aspect, the invention provides an ionic liquid of formula (2)

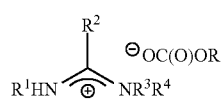

(2)

where R is alkyl, alkenyl, alkynyl, aryl, silyl, or siloxyl, and may be linear, branched, or cyclic, and may be substituted or unsubstituted; $R^2$, $R^3$, and $R^4$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si($R^6$)$_2$—O—} units; or a substituted or unsubstituted heteroaryl group optionally containing one or more {—Si $(R^6)_2$—O—} units; and $R^6$ is a substituted or unsubstituted alkyl, aryl, heteroaryl, or alkoxy moiety. In certain embodiments, $R^1$, $R^3$, and $R^4$ are not hydrogen.

In another aspect, the invention provides an ionic liquid that is made by a method comprising the steps of: mixing a compound with alcohol, water or a combination thereof, where the compound is of the formula (1):

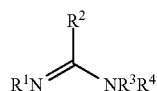
(1)

where $R^1$, $R^2$, $R^3$, and $R^4$ are independently H; a substituted or unsubstituted to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si$(R^6)_2$—O—} units; or a substituted or unsubstituted heteroaryl group optionally containing one or more {—Si$(R^6)_2$—O—} units; and $R^6$ is a substituted or unsubstituted alkyl, aryl, heteroaryl, or alkoxy moiety; contacting the mixture with carbon dioxide, $CS_2$, or COS; and obtaining the ionic liquid. In certain embodiments, $R^2$, $R^3$, and $R^4$ are not hydrogen.

In certain embodiments of the previous two aspects, the compound and the alcohol, water or combination thereof, are present in approximately equimolar amounts. In other embodiments, they are present in non-equimolar amounts.

In another aspect, the invention provides a method of making an ionic liquid, comprising the steps of: mixing a compound with alcohol, water or a combination thereof where the compound is of the formula (1):

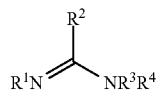
(1)

where $R^1$, $R^2$, $R^3$, and W are independently H; a substituted or unsubstituted to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si$(R^6)_2$—O—} units; or a substituted or unsubstituted heteroaryl group optionally containing one or more {—Si$(R^6)_2$—O—} units; and $R^6$ is a substituted or unsubstituted alkyl, aryl, heteroaryl, or alkoxy moiety; contacting the mixture with carbon dioxide; and obtaining the ionic liquid.

The alcohol may be ROH, where R is alkyl, alkenyl, alkynyl, aryl, silyl, or siloxyl, and may be linear, branched, or cyclic, and may be substituted or unsubstituted. The alcohol may be a primary or a secondary alcohol.

In another aspect, the invention provides a method of separating a solute from an alcoholic solution comprising the steps of: adding to an alcoholic solution comprising a solute an amount of a compound of formula (1) that is about equimolar to the amount of alcohol in the alcoholic solution; contacting the resulting mixture with carbon dioxide to convert the mixture to a first component of ionic liquid and a second component of solute; and separating the first and second components to isolate the solute.

In a further aspect, the invention provides a method for separating a desired liquid from a mixture of an alcohol and the desired liquid, comprising the steps of: adding a compound of formula (1) to a mixture of an alcohol and a desired liquid; contacting the mixture with carbon dioxide to convert the alcohol and the compound to an ionic liquid; and separating the ionic liquid and the desired liquid to isolate the desired liquid, wherein the desired liquid is not reactive with the compound in the presence of the carbon dioxide.

In another aspect, the invention provides a method for separating a desired liquid from a mixture of water and the desired liquid, comprising the steps of: adding a compound of formula (1) to a mixture of water and the desired liquid; contacting the mixture with carbon dioxide to convert the water and the compound to an ionic liquid; and separating the ionic liquid and the desired liquid to isolate the desired liquid, wherein the desired liquid is not reactive with the compound in the presence of the carbon dioxide.

In another aspect, the invention provides a method for converting an ionic liquid to a nonionic liquid, comprising the steps of: providing an ionic liquid of formula (2), where $R^1$, $R^3$, and $R^4$ are not H, removing carbon dioxide from the ionic liquid; and obtaining the nonionic liquid. Removing carbon dioxide may comprise one or more of: heating the ionic liquid, and contacting the ionic liquid with a nonreactive gas that contains insufficient $CO_2$, $CS_2$, or COS to sustain the ionic liquid in its ionic form, e.g., a nonreactive gas that contains substantially no $CO_2$, $CS_2$, or COS.

In a further aspect, the invention provides an ionic liquid having the formula (2), wherein the ionic liquid reversibly converts to a nonionic liquid when carbon dioxide is removed, and wherein the nonionic liquid converts to the ionic liquid upon contact with carbon dioxide. Carbon dioxide may be removed by contacting the ionic liquid with a gas that contains substantially no carbon dioxide. Carbon dioxide may be removed by contacting the ionic liquid with a nonreactive gas that contains insufficient $CO_2$, $CS_2$, or COS to sustain the ionic liquid in its ionic form, such as, for example, a gas that contains substantially no $CO_2$, $CS_2$, or COS.

In yet a further aspect, the invention provides an ionic liquid of formula (4)

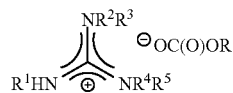
(4)

where R is alkyl, alkenyl, alkynyl, aryl, silyl, siloxyl, and may be linear, branched, cyclic, and may be substituted or unsubstituted; $R^1$, $R^2$, $R^3$, $R^4$, and $R^5$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si$(R^6)_2$—O—} units; or a substituted or unsubstituted heteroaryl group optionally containing one or more {—Si$(R^6)_2$—O—} units; and $R^6$ is a substituted or unsubstituted alkyl, aryl, heteroaryl, or alkoxy moiety. In certain embodiments, R, $R^1$, $R^2$, $R^3$, $R^4$, and $R^5$ are not hydrogen.

In a further aspect, the invention provides an ionic liquid that is made by a method comprising the steps of: mixing a compound with an alcohol, water or a combination thereof, where the compound is of the formula (3):

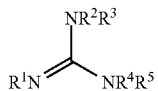

(3)

where $R^1$, $R^2$, $R^3$, $R^4$ and $R^5$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more (—Si($R^6$)$_2$—O—) units; or a substituted or unsubstituted heteroaryl group optionally containing one or more (—Si($R^6$)$_2$—O—) units; and $R^6$ is a substituted or unsubstituted alkyl, aryl, heteroaryl, or alkoxy moiety; contacting the mixture with carbon dioxide, $CS_2$, or COS, and obtaining the ionic liquid. In certain embodiments, $R^1$, $R^2$, $R^3$, $R^4$, and $R^5$ are not hydrogen.

In certain embodiments of the previous two aspects, the compound and the alcohol, water or combination thereof, are present in approximately equimolar amounts. In other embodiments, they are present in non-equimolar amounts.

In another aspect, the invention provides a method of making an ionic liquid, comprising the steps of: mixing a compound with alcohol, water or a combination thereof where the compound is of the formula (3):

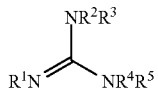

(3)

where $R^1$, $R^2$, $R^3$, $R^4$, and $R^5$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more (—Si($R^6$)$_2$—O—) units; or a substituted or unsubstituted heteroaryl group optionally containing one or more {—Si($R^6$)$_2$—O—} units; and $R^6$ is a substituted or unsubstituted alkyl, aryl, heteroaryl, or alkoxy moiety; contacting the mixture with carbon dioxide; and obtaining the ionic liquid.

The alcohol may be ROH, where R is alkyl, alkenyl, alkynyl, aryl, silyl, or siloxyl, and may be linear, branched, or cyclic, and may be substituted or unsubstituted. The alcohol may be a primary or a secondary alcohol.

In another aspect, the invention provides a method of separating a solute from an alcoholic solution comprising the steps of: adding to an alcoholic solution comprising a solute an amount of a compound of formula (3) that is about equimolar to the amount of alcohol in the alcoholic solution; contacting the resulting mixture with carbon dioxide to convert the mixture to a first component of ionic liquid and a second component of solute; and separating the first and second components to isolate the solute.

In another aspect, the invention provides a method for separating a desired liquid from a mixture of an alcohol and the desired liquid, comprising the steps of: adding a compound of formula (3) to a mixture of an alcohol and a desired liquid; contacting the mixture with carbon dioxide to convert the alcohol and the compound to an ionic liquid; separating the ionic liquid and the desired liquid to isolate the desired liquid, wherein the desired liquid is not reactive with the compound in the presence of the carbon dioxide.

In another aspect, the invention provides a method for separating a desired liquid from a mixture of water and the desired liquid, comprising the steps of: adding a compound of formula (3) to a mixture of water and the desired liquid; contacting the mixture with carbon dioxide to convert the water and the compound to an ionic liquid; and separating the ionic liquid and the desired liquid to isolate the desired liquid, wherein the desired liquid is not reactive with the compound in the presence of the carbon dioxide.

In a further aspect, the invention provides a method for converting an ionic liquid to a nonionic liquid, comprising the steps of: providing an ionic liquid of formula (4) or an ionic liquid made from the compound of formula (3), where R, $R^1$, $R^2$, $R^3$, $R^4$, and $R^5$ are not H, removing carbon dioxide from the ionic liquid; and obtaining the nonionic liquid. Removing carbon dioxide may comprise one or more of: heating the ionic liquid, and contacting the ionic liquid with a nonreactive gas that contains insufficient $CO_2$, $CS_2$, or COS to sustain the ionic liquid in its ionic form, e.g., a nonreactive gas that contains substantially no $CO_2$, $CS_2$, or COS.

In a further aspect, the invention provides an ionic liquid having the formula (4), wherein the ionic liquid reversibly converts to a nonionic liquid when carbon dioxide is removed, and wherein the nonionic liquid converts to the ionic liquid upon contact with carbon dioxide. Carbon dioxide may be removed by contacting the ionic liquid with a gas that contains substantially no carbon dioxide. Carbon dioxide may be removed by contacting the ionic liquid with a nonreactive gas that contains insufficient $CO_2$, $CS_2$, or COS to sustain the ionic liquid in its ionic form, such as, for example, a gas that contains substantially no $CO_2$, $CS_2$, or COS.

In yet a further aspect, the invention provides use of an ionic liquid of formula (2), (4) or (6), or made from a compound of formula (1), (3) or (5), as a sensor of $CO_2$, $CS_2$, or COS.

In a further aspect, the invention provides use of an ionic liquid of formula (2), (4) or (6), or made from a compound of formula (1), (3) or (5), as a detector of $CO_2$, $CS_2$, or COS.

In a further aspect, the invention provides use of an ionic liquid of formula (2), (4) or (6), or made from a compound of formula (1), (3) or (5), as a chemical switch.

In a further aspect, the invention provides use of an ionic liquid of formula (2), (4) or (6), or made from a compound of formula (1), (3) or (5), to conduct electricity.

In another aspect, the invention provides an ionic liquid of formula (6)

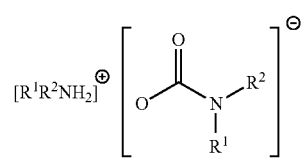

(6)

where $R^1$ and $R^2$ are independently a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si($R^6$)$_2$—O—} units;

or a substituted or unsubstituted heteroaryl group optionally containing one or more {—Si(R$^6$)$_2$—O—} units; and R$^6$ is a substituted or unsubstituted alkyl, aryl, heteroaryl, or alkoxy moiety.

In another aspect, the invention provides an ionic liquid that is made by a method comprising the steps of: contacting a compound of formula (5) with carbon dioxide, CS$_2$, or COS:

R$^1$R$^2$NH     (5)

where R$^1$ and R$^2$ are independently a substituted or unsubstituted C$_1$ to C$_{10}$ alkyl group that is linear, branched, or cyclic; a substituted or unsubstituted C$_n$Si$_m$ group where n and m are independently a number from 0 to 10 and n+m is a number from 1 to 10; a substituted or unsubstituted aryl group optionally containing one or more {—Si(R$^6$)$_2$—O—} units; or a substituted or unsubstituted heteroaryl group optionally containing one or more {—Si(R$^6$)$_2$—O—} units; and R$^6$ is a substituted or unsubstituted alkyl, aryl, heteroaryl, or alkoxy moiety; and obtaining the ionic liquid.

In certain embodiments of the previous aspect, at least one of R$^1$ and R$^2$ is lower alkyl. In one embodiment, R$^1$ is butyl and R$^2$ is ethyl.

In a further aspect, the invention provides a method of making an ionic liquid, comprising the steps of: contacting a compound of formula (5) with carbon dioxide:

R$^1$R$^2$NH     (5)

where R$^1$, and R$^2$ are independently a substituted or unsubstituted C$_1$ to C$_{10}$ alkyl group that is linear, branched, or cyclic; a substituted or unsubstituted C$_n$Si$_m$ group where n and m are independently a number from 0 to 10 and n+m is a number from 1 to 10; a substituted or unsubstituted aryl group optionally containing one or more {—Si(R$^6$)$_2$—O—} units; or a substituted or unsubstituted heteroaryl group optionally containing one or more {—Si(R$^6$)$_2$—O—} units; and R$^6$ is a substituted or unsubstituted alkyl, aryl, heteroaryl, or alkoxy moiety; and obtaining the ionic liquid.

In another aspect, the invention provides a method of isolating a solute comprising the steps of: adding a liquid compound of formula (5) to a composition comprising a solute; contacting the mixture with carbon dioxide to convert the mixture to at least a first component of ionic liquid and a second component of solute that is not soluble in the ionic liquid; and isolating the solute.

In another aspect, the invention provides a method for separating a desired liquid from a mixture comprising a compound of formula (5) and the desired liquid, comprising the steps of: contacting the mixture with carbon dioxide to convert the compound to an ionic liquid; and separating the ionic liquid and the desired liquid to isolate the desired liquid, wherein the desired liquid is not reactive with the compound in the presence of the carbon dioxide.

In a further aspect, the invention provides a method for converting an ionic liquid to a nonionic liquid, comprising the steps of: providing an ionic liquid of formula (6), removing carbon dioxide from the ionic liquid; and obtaining the nonionic liquid.

In an embodiment of the previous aspect, removing carbon dioxide comprises one or more of: heating the ionic liquid, and contacting the ionic liquid with a nonreactive gas that contains insufficient carbon dioxide to sustain the ionic liquid in its ionic form.

In another aspect, the invention provides an ionic liquid having the formula (6), wherein the ionic liquid reversibly converts to a nonionic liquid when carbon dioxide is removed, and wherein the nonionic liquid converts to the ionic liquid upon contact with carbon dioxide. Carbon dioxide may be removed by contacting the ionic liquid with a nonreactive gas that contains insufficient carbon dioxide to sustain the ionic liquid in its ionic form.

In another aspect, the invention provides a method of synthesizing polymer comprising the steps of: adding monomer and initiator to a switchable solvent in its nonionic state to form a solution; allowing the monomer and initiator to react to form dissolved polymer in solution; contacting the solution with carbon dioxide to obtain ionic liquid in which the polymer is not soluble; and isolating the polymer. A non-reactive solvent may be added to decrease viscosity of the mixture.

In certain embodiments, the previous aspect also comprises the step of contacting with carbon dioxide the ionic liquid from which polymer has been isolated to restore the switchable solvent to the nonionic state.

The polymer produced may be polystyrene.

In certain embodiments, the switchable solvent is amidine and alcohol; amidine and water; amidine and alcohol and water; guanidine and alcohol; guanidine and water; guanidine and alcohol and water, primary amine; secondary amine; or tertiary amine. In some embodiments, the switchable solvent is amidine and alcohol; amidine and water; or amidine and alcohol and water; and the amidine is a compound of formula (1). In other embodiments the switchable solvent is guanidine and alcohol; guanidine and water; or guanidine and alcohol and water; and the guanidine is a compound of formula (3). In other embodiments, the switchable solvent is an amine, preferably a secondary amine of formula (5).

In another aspect, the invention provides a polymer made by the foregoing methods. As used herein, "polymer" is intended to have a broad meaning, and encompasses homopolymers, copolymers, terpolymers, etc.

BRIEF DESCRIPTION OF THE DRAWINGS

Embodiments of the invention will now be described, by way of example, with reference to the accompanying drawings.

FIG. 7 shows NMR characterization data for N,N,N',N'-tetramethyl-N"-phenylguanidine and its bicarbonate salt.

BRIEF DESCRIPTION OF THE TABLES

Figure 1:
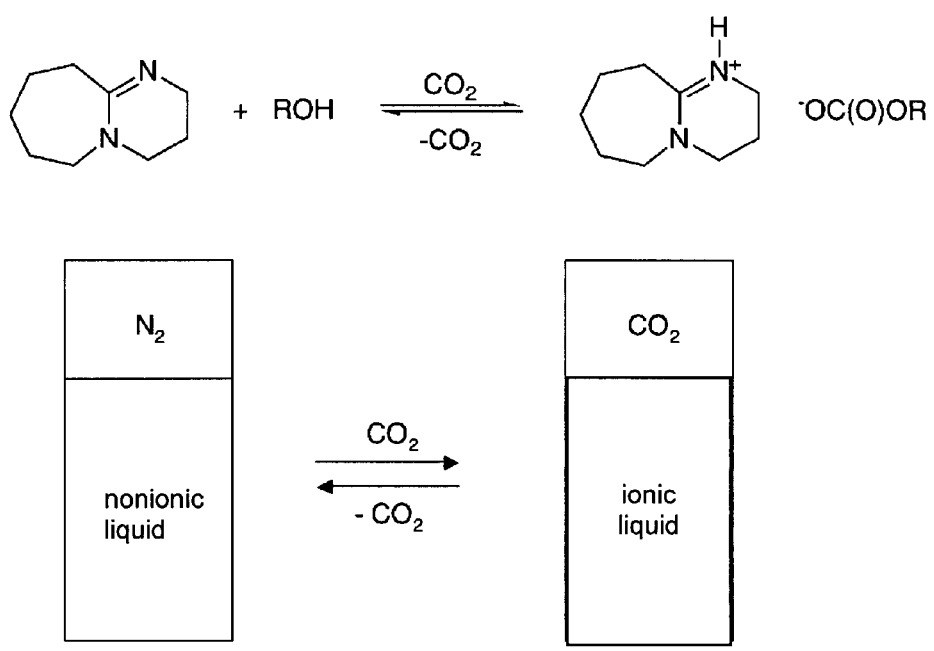
FIG. 1 shows a chemical reaction equation and a schematic of the reaction. The chemical reaction equation shows DBU (1,8-diazabicyclo-[5.4.0]-undec-7-ene) and an alcohol on the left hand side and amidinium alkyl carbonate on the right hand side. This reaction can be reversed, as indicated. The schematic shows the same reaction wherein the nonpolar nonionic liquid mixture of DBU and the alcohol are on the left side under a blanket of N$_2$. The ionic liquid amidinium alkyl carbonate product is shown on the right side under a blanket of carbon dioxide.

Tables 1-15 show the results of studies conducted as described in the working examples, as follows:

Table 1. Miscibility of the [DBUH][$O_2$COR] ionic liquids with hexane, toluene and ethyl acetate (selected traditional nonpolar solvents);

Table 2. $^{13}C\{^1H\}$ NMR chemical shifts of [DBUH][$O_2$COR] salts in $CDCl_3$;

Table 3. $^{13}C\{^1H\}$ NMR chemical shifts of pure n-alcohols in $CDCl_3$;

Table 4. $^1H$ NMR chemical shifts of [DBUH][$O_2$COR] salts in $CDCl_3$;

Table 5. $^1H$ NMR chemical shifts of pure n-alcohols in $CDCl_3$;

Table 6. $^1H$ NMR chemical shifts for key protons observed in n-hexanol, DBU, and mixtures of n-hexanol and DBU;

Table 7. $^1H$ NMR spectroscopic data for amines and their carbamate salts;

Table 8. $^{13}C$ NMR spectroscopic data for amines and their carbamate salts;

Table 9. IR spectroscopic data for the carbamate salts of selected secondary amines;

Table 10. Comparison of polarities of ethylbutylamine and DBU/1-hexanol in ionic and nonionic forms to polarities of traditional solvents;

Table 11. Qualitative study of viscosity of secondary amines in the presence and absence of $CO_2$;

Table 12. Wavelengths of secondary amines in the presence and absence of $CO_2$;

Table 13. Miscibility of selected liquids in NHEtBu and its carbamate salt;

Table 14. Solubility of selected solutes in NHEtBu and in its carbamate salt; and Table 15. Solubility of selected solutes in DBU/1-propanol mixture and in its alkylcarbonate salt.

DETAILED DESCRIPTION OF THE INVENTION

As used herein, "aliphatic" refers to hydrocarbon moieties that are linear, branched or cyclic, may be alkyl, alkenyl or alkynyl, and may be substituted or unsubstituted. "Aryl" means a moiety including a substituted or unsubstituted aromatic ring, including heteroaryl moieties and moieties with more than one conjugated aromatic ring; optionally it may also include one or more non-aromatic ring. Examples of aryl moieties include, phenyl, biphenyl, naphthyl, anthryl, phenanthryl, pyrenyl, pyridyl, bipyridyl, xylyl, indolyl, thienyl, and quinolinyl.

As used herein "unsubstituted" refers to any open valence of an atom being occupied by hydrogen. For example, a person of ordinary skill in the art would understand that an unsubstituted $C_nSi_m$ group is a $C_nSi_mH_x$ group where n and m are independently a number from 0 to 10, x is any number up to 2n+2 m+2, and n+m is a number from 1 to 10.

"Substituted" means having one or more substituent moieties whose presence does not interfere with the desired reaction. Examples of substituents include alkyl, alkenyl, alkynyl, aryl, aryl-halide, heteroaryl, cyclyl (non-aromatic ring), Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof. Preferable substituents are alkyl, aryl, heteroaryl, and ether. It is noted that aryl halides are acceptable substituents. Alkyl halides are known to be quite reactive, they are acceptable so long as they do not interfere with the desired reaction.

As used herein, "heteroatom" refers to non-hydrogen and non-carbon atoms, such as, for example, O, S, and N.

"Alcohol" means a molecule of the formula ROH, where R is alkyl, alkenyl, alkynyl, aryl, silyl, or siloxyl, and may be linear, branched, cyclic, and may be substituted or unsubstituted. Substituents are as defined above and include moieties that do not interfere with the desired reaction. Alcohols for use in the invention may optionally be chiral.

The term "switched" means that the physical properties have been modified. "Switchable" means able to be converted from a first state with a first set of physical properties to a second state with a second set of physical properties. A "trigger" is a change of reaction conditions (e.g., introduction or removal of a gas) that causes a change in the physical properties. The term "reversible" means that the reaction can proceed in either direction (backward or forward) depending on the reaction conditions.

"Short chain aliphatic" or "lower aliphatic" refers to $C_1$ to $C_4$ aliphatic. "Long chain aliphatic" or "higher aliphatic" refers to $C_5$ to $C_{25}$ aliphatic. "DBU" means 1,8-diazabicyclo-[5.4.0]-undec-7-ene. As used herein, "air that has had its carbon dioxide component substantially removed" means that the air has insufficient carbon dioxide content to interfere with the removal of carbon dioxide from the solution. For some applications, untreated air may be successfully employed, i.e., air in which the carbon dioxide component is unaltered; this would provide a cost saving.

As used herein, "amidine" (picture below) refers to a molecule with a structure $R^1N=C(R^2)-NR^3R^4$, where $R^1$ through $R^4$ are aliphatic or siloxyl or aryl or aliphatic/siloxyl as discussed below. The bicarbonate salt of an amidine (picture below) is termed an "amidinium bicarbonate". An amidinium salt that has the anionic counterion $[ROCO_2^-]$ is termed an "amidinium alkylcarbonate" (picture below). It should be noted that amidine as used herein also includes the structure $R^1N=CH-NR^3R^4$ (i.e., $R^2$ is replaced by H), where $R^1$, $R^3$, and $R^4$ are as discussed below.

As used herein, "guanidine" (picture below) refers to a molecule with a structure $R^1N=C(NR^2R^3)(NR^4R^5)$ where $R^1$ through $R^5$ are aliphatic or siloxyl or aryl or aliphatic/siloxyl or aryl/siloxyl or aliphatic/aryl/siloxyl as discussed below. The bicarbonate salt of such molecule is termed the "guanidinium bicarbonate" (picture below). A guanidinium salt that has the anionic counterion $[ROCO_2^-]$ is termed "guanidinium alkylcarbonate" (picture below).

"Ionic" means containing or involving or occurring in the form of positively or negatively charged ions, i.e., charged moieties. "Zwitterionic" means having two oppositely charged groups present at different locations within the same molecule. For purposes of this disclosure, "ionic liquids" are salts that are liquid below 100° C.; such liquids are typically nonvolatile, polar and viscous. For purposes of this disclosure, "zwitterionic liquids" are zwitterionic compounds that are liquid below 100° C. "Nonionic liquids" means liquids that do not consist primarily of molecules with formal charges such as ions. Nonionic liquids are available in a wide range of polarities and may be polar or nonpolar; they are typically more volatile and less viscous than ionic liquids.

A polar molecule is a molecule in which some separation occurs of the centres of positive and negative charge, generally resulting in a region of partial positive charge and a region of partial negative charge. Polar solvents are typically characterized by a dipole moment. Ionic liquids are considered to be polar solvents (Aki, 2001; Reichardt, 2005), even though a dipole may not be present, because they behave in the same manner as polar liquids in terms of their ability to solubilize polar solutes, their miscibility with other polar liquids, and their effect on solvatochromic dyes. A polar solvent is generally better than a nonpolar (or less polar) solvent at dissolving polar or charged molecules.

"Nonpolar" means having weak solvating power of polar or charged solute molecules. Nonpolar as used herein means devoid of polarity or having low polarity. Nonpolar solvents are associated with either having little or no separation of charge, so that no positive or negative poles are formed, or having a small or zero dipole moment. A nonpolar solvent is generally better than a polar solvent at dissolving nonpolar, waxy, or oily molecules.

"NMR" means Nuclear Magnetic Resonance. "Wet diethyl ether" means diethyl ether that has been purchased from a supplier and whose container has been opened to the atmosphere such that water from the air surrounding the container has entered the solvent.

The invention provides a method of separating a solute (a dissolved compound) from solution by switching the physical properties (e.g., polarity, volatility, conductivity, etc.) of the solvent of the system. When the solvent has been converted into its second form, the solute may be separated from solution. Separation may include, for example, decanting, filtering, and centrifuging. The invention further provides a method for maintaining or disrupting miscibility of two liquids by using a reversible switchable solvent as one of the two liquids. When a trigger is applied, the switchable solvent's properties change and the newly-immiscible liquids separate. An embodiment of the invention provides a switchable solvent that can be reversibly and readily switched between nonionic liquid and ionic liquid forms by applying or removing $CO_2$, $CS_2$ or COS. In most of the discussion herein of such embodiment and other embodiments of the invention, the term "$CO_2$" will be employed though that gas may in some circumstances optionally be replaced by $CS_2$ or COS, as discussed in more detail below.

In certain embodiments of the invention, the liquid mixture is (1) amidine and alcohol, (2) amidine and water, (3) amidine, alcohol and water, (4) guanidine and alcohol, (5) guanidine and water, (6) guanidine, alcohol and water, (7) a mixture of one or more amidine and one or more guanidine and alcohol, water or a combination thereof, (8) a nitrogen-containing organic compound that is of about equal or weaker basicity than amidine (or guanidine) and alcohol, water or a combination thereof, or (9) a primary, secondary or tertiary amine.

In some embodiments of the invention, it is desirable to have the amount of amidine, guanidine or combination thereof be greater than equimolar to the amount of alcohol, water or combination thereof so that, upon exposure of the liquid mixture to $CO_2$ and after conversion of much of the liquid to ionic liquid, there remains some amidine, guanidine or combination thereof in non-ionic form. Having such remaining non-ionic component(s) in the liquid confers a practical advantage such as reduced viscosity, preferred pH, or different phase behaviour, relative to other stoichiometry (equimolar or excess alcohol, water or combination thereof).

In other embodiments of the invention, it is desirable to have the amount of amidine, guanidine or combination thereof be less than equimolar to the amount of alcohol, water or combination thereof so that, upon exposure of the liquid mixture to $CO_2$ and after conversion to ionic liquid, there remains some alcohol, water or combination thereof in non-ionic form. Similarly to the above-described embodiments, having such remaining non-ionic component(s) in the liquid confers a practical advantage such as reduced viscosity, preferred pH, or different phase behaviour, relative to other stoichiometry (equimolar or excess amidine, guanidine or combination thereof).

Even in applications where the intention is to have an equimolar mixture of amidine, guanidine or combination thereof and alcohol, water or combination thereof, it may not be necessary or practical for the mixture to be precisely equimolar. While having the mixture be exactly equimolar would allow the greatest change in physical properties upon exposure of the mixture to $CO_2$, a large change in physical properties will still be obtained with mixtures that moderately deviate from equimolar. The larger the deviation from equimolar, the smaller the expected change in physical properties of the liquid upon exposure to $CO_2$.

An amidine is depicted below,

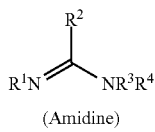

(Amidine)

where $R^1$, $R^2$, $R^3$, and $R^4$ are independently H; a substituted or unsubstituted $C_1$ to $C_{10}$ alkyl group that is linear, branched, or cyclic; a substituted or unsubstituted group where n and m are independently a number from 0 to 10 and n+m is a number from 1 to 10; a substituted or unsubstituted aryl group optionally containing one or more $\{-Si(R^6)_2-O-\}$ units; a substituted or unsubstituted heteroaryl group optionally containing one or more $\{-Si(R^6)_2-O-\}$ units; and $R^6$ is a substituted or unsubstituted alkyl, aryl, heteroaryl, or alkoxy moiety; wherein a substituent is independently alkyl, alkenyl, alkynyl, aryl, aryl halide, heteroaryl, non-aromatic rings, $Si(alkyl)_3$, $Si(alkoxy)_3$, halo, alkoxy, amino, ester, amide, thioether, alkylcarbonate, phosphine, thioester, or a combination thereof.

In the presence of an alcohol and carbon dioxide, such an amidine converts to an amidinium alkylcarbonate as depicted below,

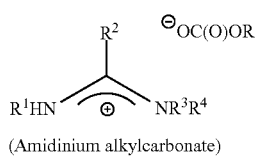

(Amidinium alkylcarbonate)

where R where R is alkyl, alkenyl, alkynyl, aryl, silyl, siloxyl, and may be linear, branched, cyclic, and may be substituted or unsubstituted;

$R^1$, $R^2$, $R^3$, and $R^4$ are as defined above.

In the presence of water and carbon dioxide, such an amidine converts to an amidinium bicarbonate as depicted below,

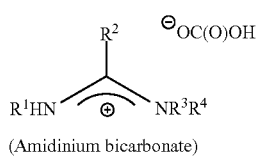

(Amidinium bicarbonate)

where $R^1$, $R^2$, $R^3$, and $R^4$ are as defined above. In the case of DBU and water in the presence of $CO_2$, solid bicarbonate forms.

A guanidine is as shown below,

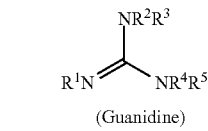

(Guanidine)

where $R^1$, $R^2$, $R^3$, $R^4$ and $R^5$ are independently H; a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more $\{-Si(R^6)_2-O-\}$ units; a substituted or unsubstituted heteroaryl group optionally containing one or more $\{-Si(R^6)_2-O-\}$ units;

$R^6$ is a substituted or unsubstituted alkyl, aryl, heteroaryl, or alkoxy moiety;

wherein a substituent is independently alkyl, alkenyl, alkynyl, aryl, aryl halide, heteroaryl, non-aromatic rings, $Si(alkyl)_3$, $Si(alkoxy)_3$, halo, alkoxy, amino, ester, amide, thioether, alkylcarbonate, phosphine, thioester, or a combination thereof.

In the presence of an alcohol and carbon dioxide, such a guanidine converts to a guanidinium alkylcarbonate as depicted below,

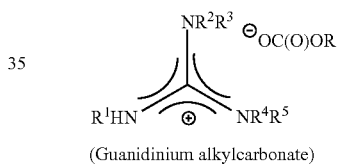

(Guanidinium alkylcarbonate)

where R is alkyl, alkenyl, alkynyl, aryl, silyl, siloxyl, and may be linear, branched, cyclic, and may be substituted or unsubstituted; and $R^1$, $R^2$, $R^3$, $R^4$ and $R^5$ are as defined above.

In the presence of water and carbon dioxide, such a guanidine converts to an guanidinium bicarbonate as depicted below,

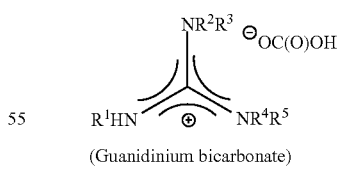

(Guanidinium bicarbonate)

where R, $R^1$, $R^2$, $R^3$, $R^4$, and $R^5$ are as defined above.

A reversibly switchable liquid solvent was formed by reacting the guanidine base N,N,N',N'-tetramethyl-N"-phenylguanidine with carbon dioxide in the presence of water (see the reaction scheme below, and Example 3). The complete reverse reaction was effected by bubbling with $N_2$, and it was verified by $^1H$ NMR that no bicarbonate remained (see FIG. 7).

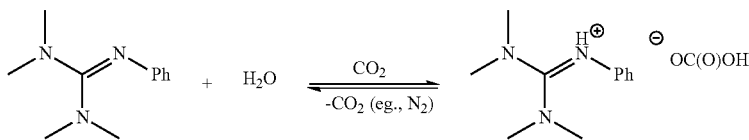

Analogously, a switchable solvent was converted by reacting the guanidine base N,N,N',N'-tetramethyl-N''-(2-fluorophenyl)guanidine with carbon dioxide in the presence of water (see the reaction scheme below, FIG. 5 and Example 3).

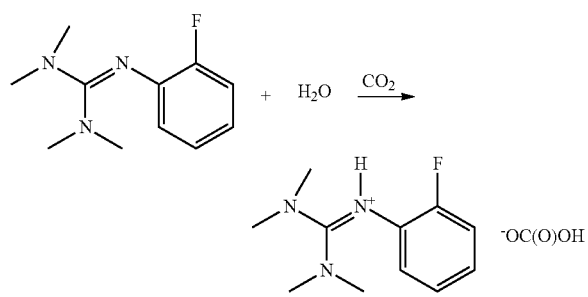

Figure 9:
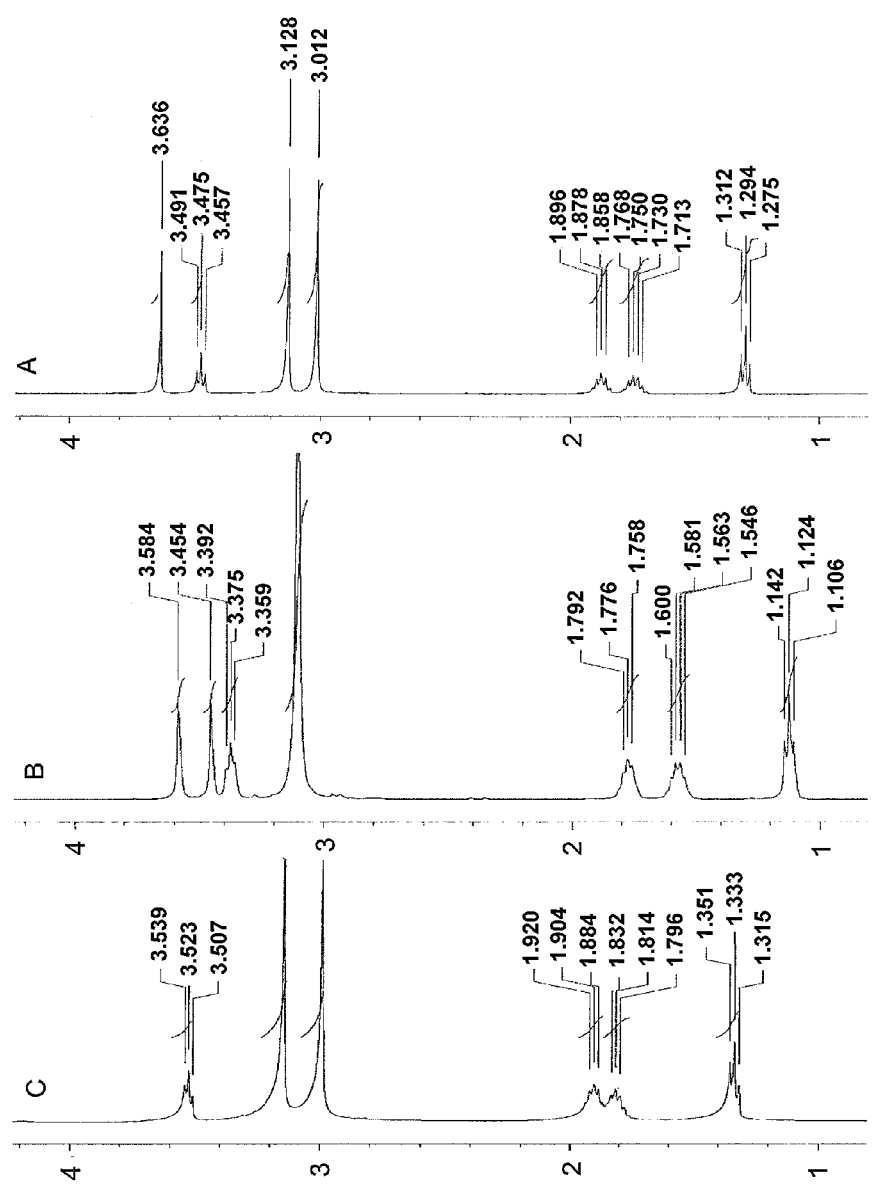
FIG. 9A shows a $^1H$ NMR spectrum of an equimolar solution of 2-butyl-1,1,3,3-tetramethylguanidine and methanol.
FIG. 9B shows the same mixture after addition of $CO_2$ and subsequent protonation of the 2-butyl-1,1,3,3-tetramethylguanidine and formation of the methyl carbonate anion.
FIG. 9C shows a $^1H$ NMR spectrum of the mixture of FIG. 9B after bubbling with nitrogen for 16 hours, indicating that the ionic liquid has reversed to its original components.

Another reversibly switchable ionic liquid was formed at room temperature by exposing an equimolar mixture of methanol and 2-butyl-1,1,3,3-tetramethylguanidine (see below where R=butyl) to gaseous $CO_2$ at one atmosphere. Reversibility of this system was demonstrated by Nuclear Magnetic Resonance ($^1$H and $^{13}$C) and conductivity studies (see FIGS. 9 and 10) as described in Example 4B. Formation of the ionic liquid occurred after bubbling $CO_2$ through a 1:1 molar ratio mixture of 2-butyl-1,1,3,3-tetramethylguanidine and methanol for 20 minutes. The ionic liquid was then converted back to 2-butyl-1,1,3,3-tetramethylguanidine and methanol by bubbling with $N_2$ or argon overnight; the ionic liquid can also be reversed solely by heat, as indicated by thermogravimetric studies (see FIG. 11). The ionic liquid underwent reversal at temperatures as low as 50° C., releasing $CO_2$ and low-boiling methanol. This system is suitable for applications where removal of the alcohol by evaporation is desirable after switching to the guanidine and alcohol.

Referring to the single component amine system of the present invention, a scheme depicting the reversible switching of secondary amines in the presence of $CO_2$ is provided below.

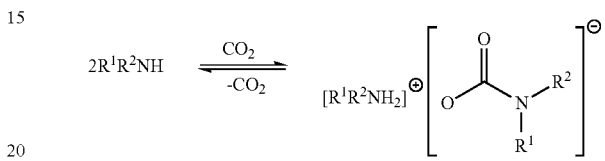

where $R^1$ and $R^2$ are independently a substituted or unsubstituted $C_1$ to $C_{10}$ alkyl group that is linear, branched, or cyclic; a substituted or unsubstituted $C_nSi_m$ group where n and m are independently a number from 0 to 10 and n+m is a number from 1 to 10; a substituted or unsubstituted aryl group optionally containing one or more {—Si($R^6$)$_2$—O—} units; or a substituted or unsubstituted heteroaryl group optionally containing one or more {—Si($R^6$)$_2$—O—} units; and $R^6$ is a substituted or unsubstituted alkyl, aryl, heteroaryl, or alkoxy moiety.

Tertiary amines may be switched once (from nonionic to ionic) but in general are not suited to reversibility as they lack an N—H bond into which $CO_2$ can be inserted. Although primary amines give solid carbamate salts at room temperature, they are well suited to serve as switchable solvents at higher temperatures where their carbamate salts are liquid. Secondary amines are particularly preferred as reversibly switchable solvents as there are many examples of secondary amines with nonionic and ionic forms that are liquid at room temperature. However, in general, secondary amines have some toxicity and would not be suitable for use as solvents, for example, for food preparation.

N-butyl-N-ethylamine (NHEtBu) is an exemplary switchable solvent that uses the same benign triggers as amidine

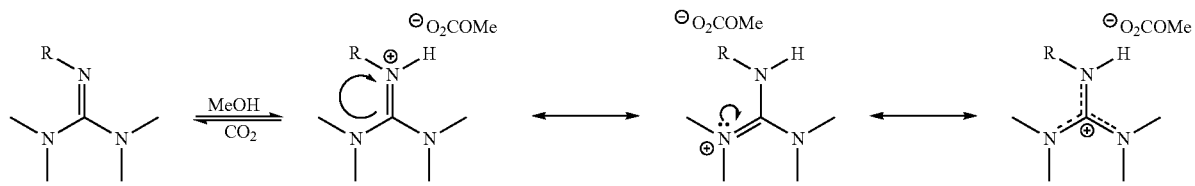

Amines employed as single component systems are also suitable as switchable solvents. Primary and secondary amines are preferred; secondary amines are particularly preferred. Such systems, relative to DBU/ROH systems, generally have decreased sensitivity to moisture. Single component systems are attractive due to cost effectiveness, decreased number of components for undesired side reactions, and convenient operation in industrial applications. The reaction of primary amines together with DBU and $CO_2$ and has recently been investigated by Weiss's research group and is described in Yamada et al. (2007).

and/or guanidine/alcohol mixtures. Unlike such mixtures, NHEtBu is water-insensitive, is less expensive than amidines, and has a significantly less polar low-polarity form.

NHEtBu is used as a model for many of the secondary amine studies described herein. It is a switchable solvent that switches from very low polarity when under air to much higher polarity when $CO_2$ is bubbled through it. The polar form is believed to be primarily the carbamate salt (N,N-butylethyl-ammonium N',N'-butylethylcarbamate), although in the presence of water there may be some bicarbonate salt. Initial experiments with secondary amines show that the presence of moisture does not interfere with the switchable reaction unless there is a very large amount of water such as one mole of water per mole of amine. If there is a large amount of water, a white solid is obtained which appears, by spectroscopy, to be the bicarbonate salt.

Studies were conducted using NHEtBu and carbon dioxide to reversibly form an ionic liquid. Various solids were tested for their solubility in NHEtBu and its carbamate salt (see Table 14). Particularly low polarity solids were soluble in only NHEtBu, while solids of higher polarity were either soluble in both or only soluble in the carbamate. Solids of very high polarity or hydrophilicity were soluble in neither form. Various liquids, including toluene, mesitylene, propylene carbonate, styrene, decane, 5-trans-decene, hexadecane and water, were found to be miscible with both NHEtBu and its carbamate salt (see Table 13). Stilbene, in contrast, was miscible with NHEtBu and immiscible with the carbamate.

Figure 15:
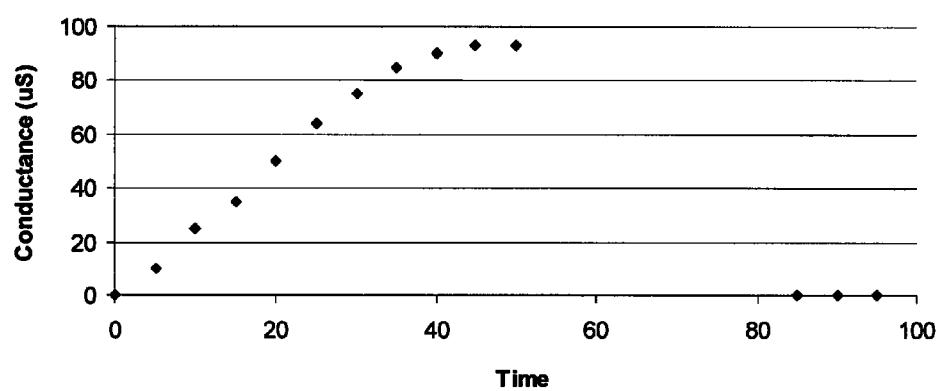
FIG. 15 graphically presents conductivity of neat ethylbutylamine where carbon dioxide is added at room temperature (from 0 to 55 minutes), and where $N_2$ is added (from 55 to 100 minutes, 55° C.).

Conductivity of NHEtBu was studied in the presence of $CO_2$ and $N_2$; results are depicted in FIG. 15. A small amount of water in NHEtBu does not impede its reversibility. An equimolar amount of water in NHEtBu results in creation of solid bicarbonate salt when $CO_2$ is bubbled through the mixture. Confirmation of the identification of the white precipitate was obtained from its IR peak at 836 $cm^{-1}$ (bicarbonate out-of-plane vibration).

Polarities of secondary amines in their amine and carbamate forms were determined using the solvatochromic probe Nile Red and are reported as wavelength values ($\lambda$, nm). As shown in Table 12, NHEtBu has a very low polarity, lower than that of ethyl acetate, but after conversion of the amine to the carbamate the polarity rises to become comparable to acetone. The viscosity also visibly increases during the $CO_2$ treatment as seen in Table 11. Bubbling nitrogen through the carbamate ionic liquid for 2.5 h converted it back to low polarity again, as shown by the (reformed) nonionic liquid's wavelength value.

N-benzylmethylamine (NHBzMe) is a significantly more polar secondary amine than NHEtBu. Otherwise it behaves similarly; $CO_2$ exposure caused an increase in polarity and viscosity while treatment with $N_2$ at 60° C. reversed that change. The final $\lambda_{max}$ is slightly higher (536 nm) than the original value for NHBzMe before exposure to $CO_2$. The two forms of NHBzMe almost exactly match the polarities of the two forms of DBU/1-hexanol.

Secondary amines or protonated secondary amines may react with aldehydes or ketones to create iminium cations, a reaction that is not possible in the amidine/ROH or guanidine/ROH switchable solvents. In most applications of switchable solvents, such reactivity is undesirable. However, in some applications it can be advantageous, for example, reactions of unsaturated aldehydes that are promoted by iminium cation formation (see Jen et al. 2000).

Secondary amines that are volatile (i.e., having boiling points below about 100° C.) will suffer evaporative losses during the switching off process. That is, the use of heat and/or flushing gas to flush away the $CO_2$ will also cause a significant portion of the secondary amine to evaporate. For this reason, less volatile secondary amines are preferred.

Referring to FIG. 1, a chemical scheme and schematic drawing are shown for a switchable solvent system of the amidine DBU and an alcohol (see Example 1).

Figure 2:
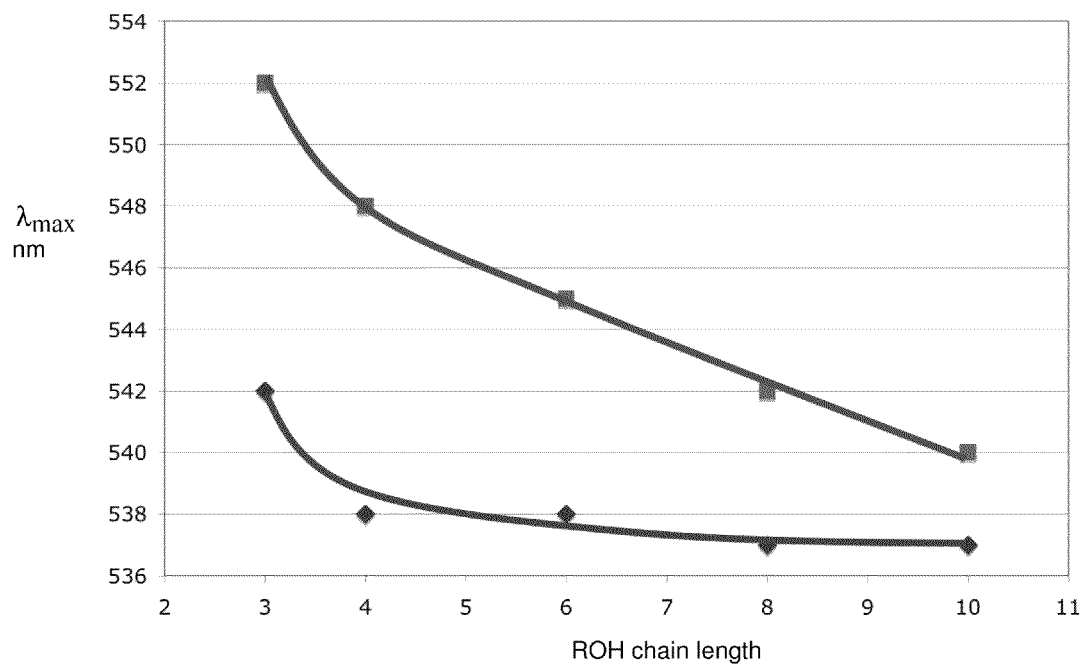
FIG. 2 graphically presents the polarity of nonionic liquid mixtures of equimolar amounts of DBU and C$_3$ to C$_{10}$ alcohols in the lower curve (◆); and the polarity of the corresponding ionic liquids that result from reaction of the liquid mixtures with CO$_2$ gas at 1 bar, in the upper curve (■). The polarity is indicated by the wavelength of maximum absorbance of dissolved solvatochromic dye Nile Red.

FIG. 2 graphically depicts the polarity of the nonionic liquid mixtures of DBU and C1 to C10 n-alcohols and the ionic liquids formed after exposure to carbon dioxide. The graph in FIG. 2 conveys polarity by displaying the wavelength of maximum absorbance of dissolved solvatochromic dye Nile Red for each system. A larger wavelength indicates greater polarity of the system.

Figure 3:
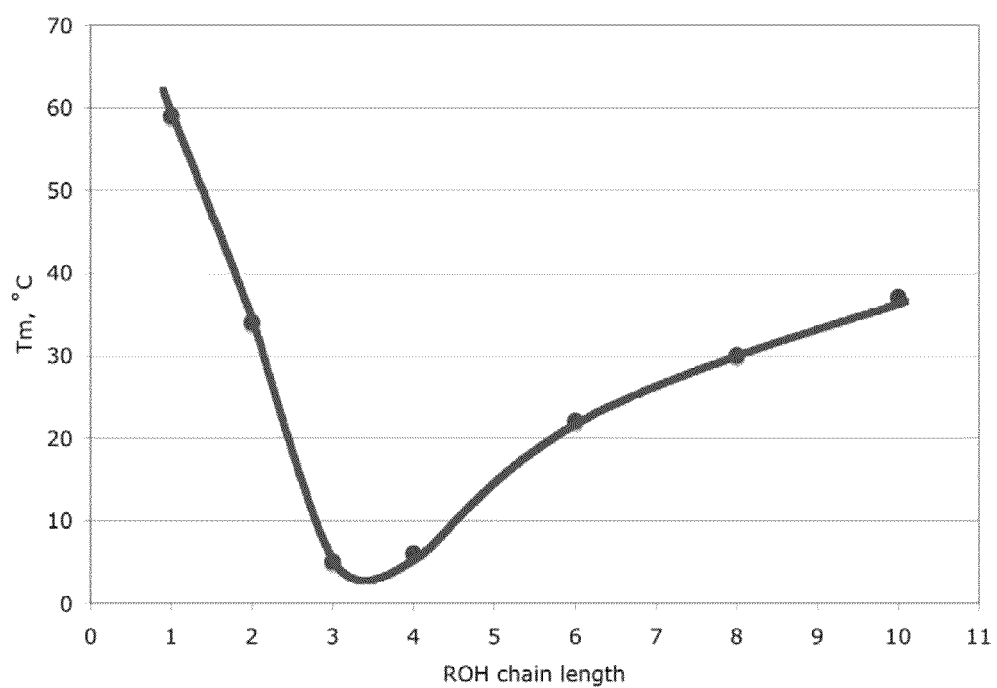
FIG. 3 graphically presents the melting temperature of ionic liquids that are formed by the reaction of CO$_2$ with equimolar mixtures of DBU and C1 to C10 alcohols.

FIG. 3 shows the melting temperature of ionic liquids formed by reacting $CO_2$ with equimolar mixtures of DBU with n-alcohols of varying lengths of carbon chains, as indicated.

Figure 4:
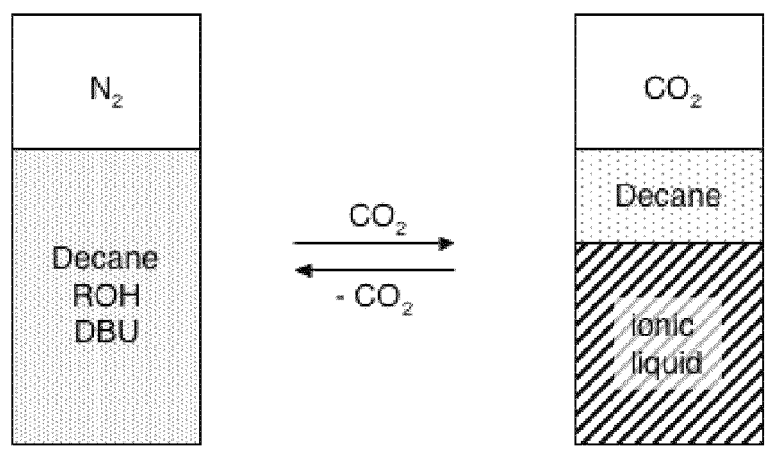
FIG. 4 shows a schematic of the miscibility test described in Example 2 wherein decane is miscible with alcohol and DBU on the left side and is immiscible with the corresponding ionic liquid, [DBUH$^+$][RCO3$^-$], on the right side. This separation is reversible as indicated.

FIG. 4 shows a schematic of the miscibility of decane with the nonionic and ionic forms of DBU and alcohol. The nonionic liquid mixture is miscible with decane. The ionic liquid is immiscible with decane. This separation is reversible as indicated. The same behaviour was observed with hexane in place of decane for a DBU/alcohol system. It was observed that the chosen alcohol must not have too long an alkyl chain, or such separation will not be observed; the alcohol's alkyl chain must be shorter than 10 carbons for the ionic form to be immiscible with hexane.

Figure 5A:
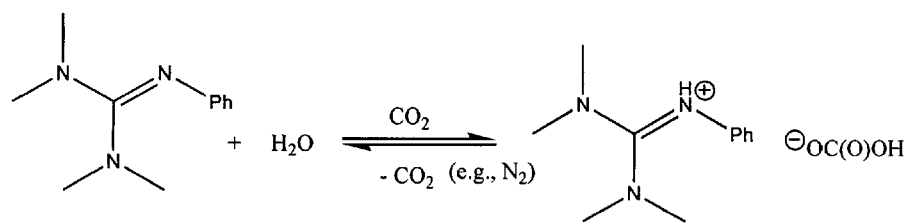
FIG. 5A shows a chemical scheme of N,N,N',N'-tetramethyl-N''-phenylguanidine and water reversibly reacting with carbon dioxide to form the corresponding guanidinium bicarbonate, which is an ionic liquid.
Figure 5B:
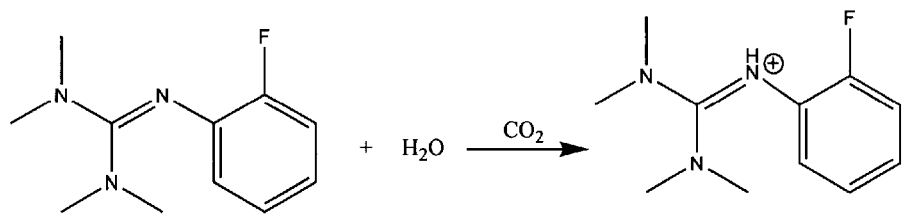
FIG. 5B shows a chemical scheme of N,N,N',N'- tetramethyl-N"-(2-fluorophenyl) guanidine and water reacting with carbon dioxide to form the corresponding guanidinium bicarbonate, which is also an ionic liquid.
Figure 5C:
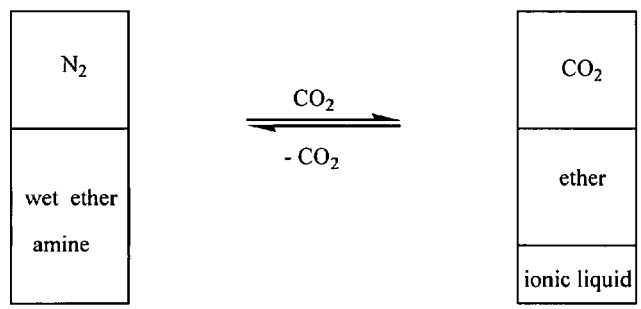
FIG. 5C shows a schematic of such reactions as described in Example 3, wherein the guanidine in each case (denoted as "amine") is miscible with wet ether on the left side, and the guanidinium bicarbonate separates from the ether into the ionic liquid on the right side.

FIG. 5A shows a chemical scheme of N,N,N',N'-tetramethyl-N''-phenylguanidine and water reacting with carbon dioxide to form the corresponding guanidinium bicarbonate. FIG. 5B shows a chemical scheme of N,N,N',N'-tetramethyl-N''-(2-fluorophenyl)guanidine and water reacting with carbon dioxide to form the corresponding guanidinium bicarbonate. A schematic at FIG. 5C depicts the experiment described in Example 3 where the guanidine and wet diethyl ether react with carbon dioxide to form a liquid ionic salt at the bottom of the vessel and diethyl ether at the top of the vessel, under a blanket of $CO_2$. This reaction is not reversible by the simple application of $N_2$ or argon.

Figure 6A:
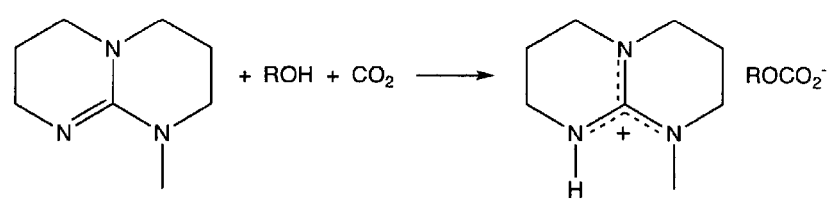
FIG. 6A shows a chemical scheme of Me-MTBD and alcohol reacting with $CO_2$ to form the corresponding ionic liquid.
Figure 6B:
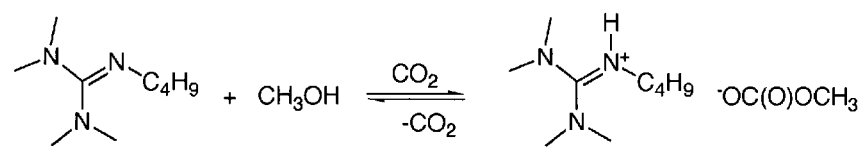
FIG. 6B shows a chemical scheme of N,N,N',N'-tetramethyl-N"-butylguanidine and methanol reacting with $CO_2$ to form the corresponding ionic liquid.

FIG. 6A shows a chemical scheme of 1,3,4,6,7,8-hexahydro-1-methyl-2H-pyrimido[1,2-a]pyrimidine "Me-MTBD" in alcohol reacting with $CO_2$ to form the corresponding salt (1,3,4,6,7,8-hexahydro-1-methyl-2H-pyrimido[1,2-a]pyrimidinium hexylcarbonate). This reaction is not reversible by the simple application of heat. FIG. 6B shows a chemical scheme of N,N,N',N'-tetramethyl-N''-butylguanidine and methanol reacting with $CO_2$ to form the corresponding ionic liquid.

FIG. 7 shows NMR characterization data for N,N,N',N'-tetramethyl-N''-phenylguanidine and its bicarbonate salt.

Figure 8:
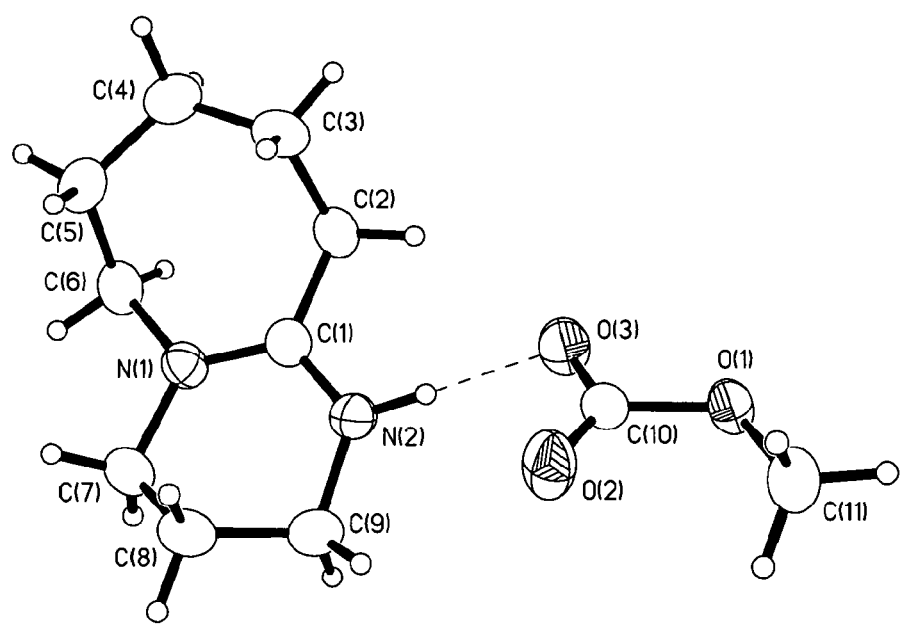
FIG. 8 shows an x-ray crystal structure of [DBUH][$O_2$COMe].

FIG. 8 shows an x-ray crystal structure of [DBUH] [$O_2$COMe]. Details of the data collection are provided in Example 9. This structure is provided as further proof of the structure of the salt that is formed by bubbling $CO_2$ through a mixture of DBU and alcohol. Methanol was used for the formation of the studied crystal since $CO_2$ in a DBU/MeOH system produces a salt in solid form.

FIG. 9A shows a $^1H$ NMR spectrum of an equimolar solution of 2-butyl-1,1,3,3-tetramethylguanidine and methanol. FIG. 9B shows the same mixture after addition of $CO_2$ and subsequent protonation of the 2-butyl-1,1,3,3-tetramethylguanidine and formation of the methyl carbonate anion. FIG. 9C shows a $^1H$ NMR spectrum of the mixture of 9B after bubbling with nitrogen for 16 hours, indicating that the ionic liquid has reversed to its original components.

Figure 10:
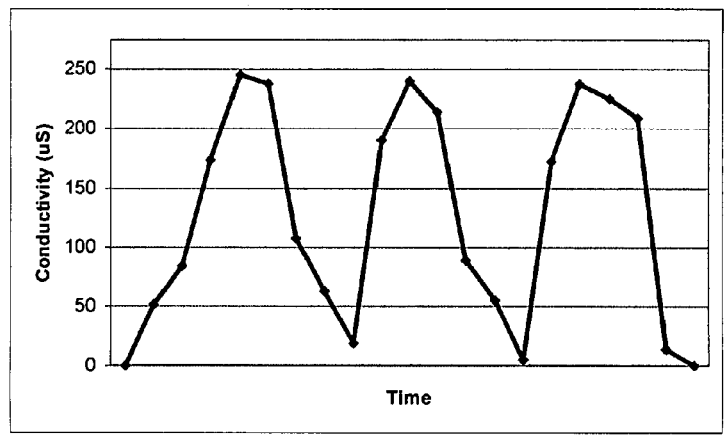
FIG. 10 graphically presents the change in conductivity of an equimolar mixture of methanol and 2-butyl-1,1,3,3-tetramethylguanindine in chloroform. The conductivity was switched on by bubbling the mixture with $CO_2$ to form an ionic liquid; the conductivity was switched off by applying heat (80° C.).

FIG. 10 graphically presents the change in conductivity of an equimolar mixture of methanol and 2-butyl-1,1,3,3-tetramethylguanindine in chloroform. The conductivity was switched on by bubbling the mixture with $CO_2$ to form an ionic liquid; the conductivity was switched off by applying heat (80° C.).

Figure 11:
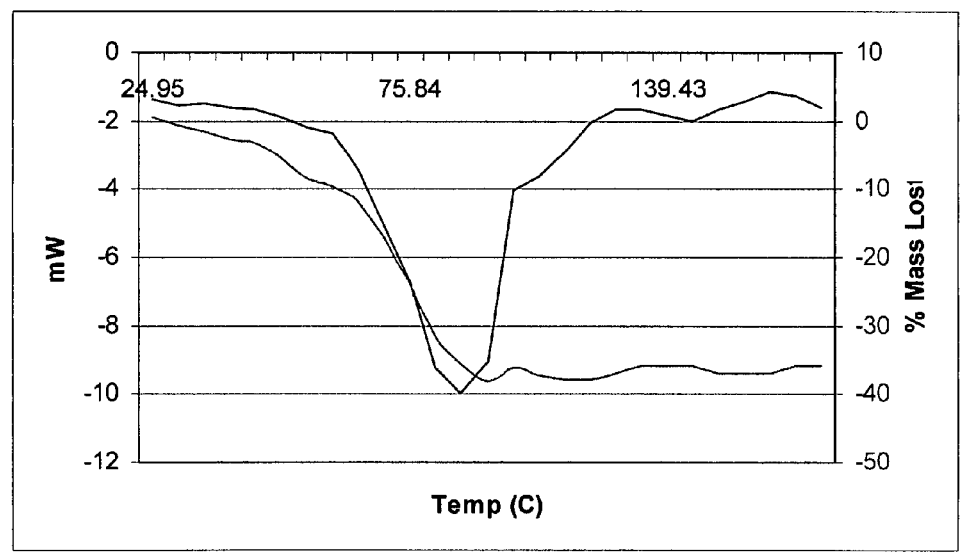
FIG. 11 graphically presents thermogravimetric analysis of 2-butyl-1,1,3,3-tetramethylguanindinium methycarbonate. This graph plots heat flow in milliwatts against temperature (° C.) and against percentage mass lost.

FIG. 11 graphically presents thermogravimetric analysis of 2-butyl-1,1,3,3-tetramethylguanindinium methycarbonate. This graph plots heat flow in milliwatts against temperature (° C.) and against percentage mass lost. This graph indicates that a percentage of mass was lost from the sample that is consistent with loss of $CO_2$ and methanol. The mass loss began at approximately 50° C.

Figure 12A:
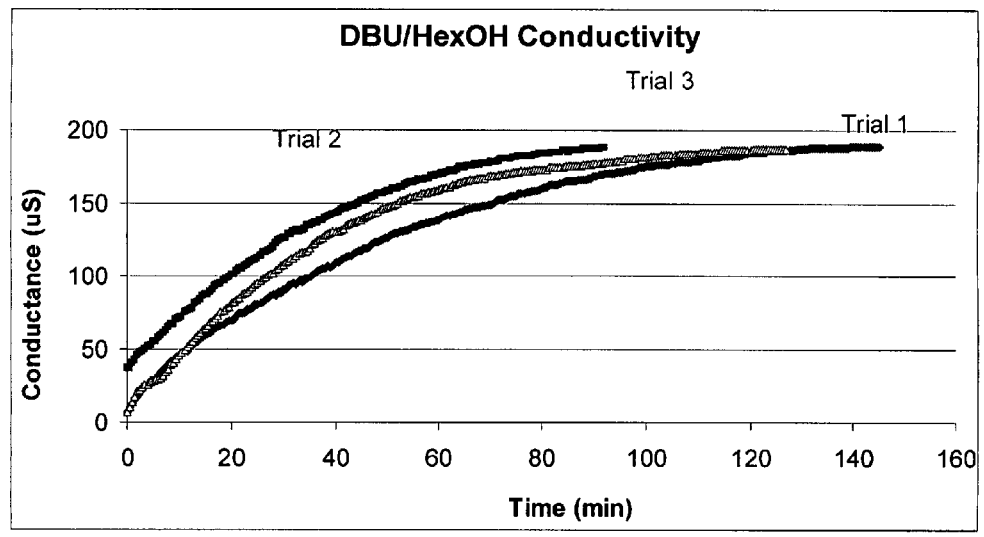
FIG. 12A graphically presents the change in conductivity of a neat DBU/hexanol mixture during $CO_2$ bubbling: three trials are presented to show reproducibility.
Figure 12B:
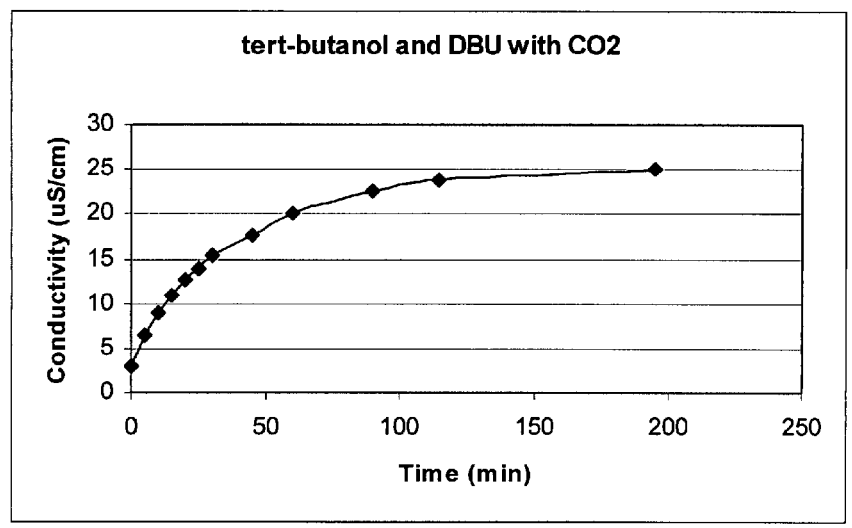
FIG. 12B graphically presents the change in conductivity of a neat tert-butanol/DBU mixture during $CO_2$ bubbling.

FIG. 12A graphically presents the change in conductivity of a neat DBU/hexanol mixture during $CO_2$ bubbling. Three trials are presented to show reproducibility. FIG. 12B graphically presents the change in conductivity of a neat tert-butanol/DBU mixture during $CO_2$ bubbling.

Figure 13:
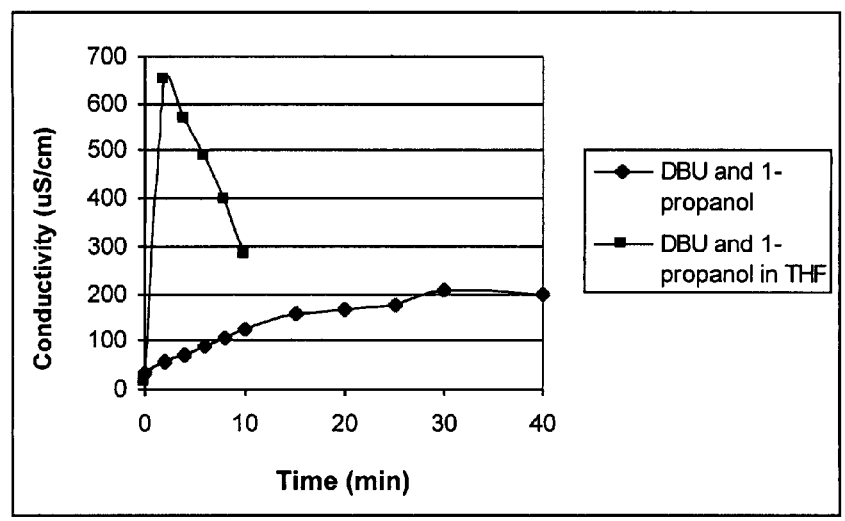
FIG. 13 graphically presents the change in conductivity over time for DBU/1-propanol, and DBU/1-propanol in THF.

FIG. 13 graphically presents the change in conductivity over time for DBU/1-propanol, and DBU/1-propanol in THF.

Figure 14A:
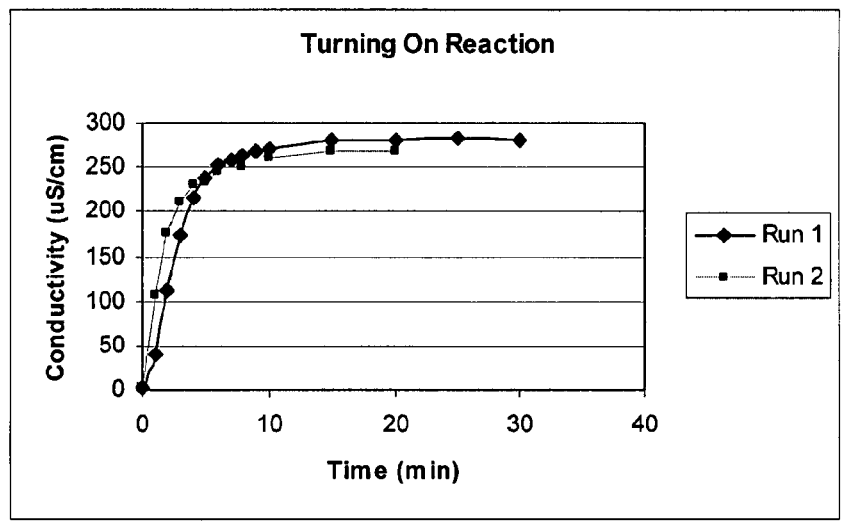
FIG. 14A graphically presents the change in conductivity over time for DBU/1-hexanol in toluene with $CO_2$ bubbling. Two trials are presented to show reproducibility.
Figure 14B:
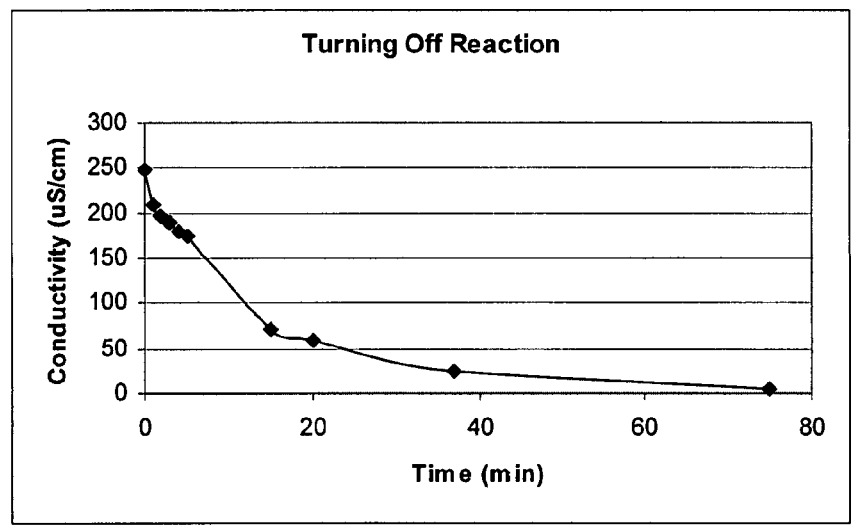
FIG. 14B graphically presents the change in conductivity over time for DBU/1-hexanol in toluene in the presence of $N_2$.

FIG. 14A graphically presents the change in conductivity over time for DBU/1-hexanol in toluene with $CO_2$ bubbling. Two trials are presented to show reproducibility. FIG. 14B graphically presents the change in conductivity over time for DBU/1-hexanol in toluene in the presence of $N_2$.

FIG. 15 graphically presents conductivity of neat ethylbutylamine where carbon dioxide is added at room temperature (from 0 to 55 minutes), and where $N_2$ is added (from 55 to 100 minutes, 55° C.).

As described in the working examples, several ionic liquids have been formed according to the invention by reacting carbon dioxide with amidines or guanidines and alcohols or water. An advantage of the alcohol system is that the reverse reactions are readily effected by removing the carbon dioxide from the ionic liquid by flushing the system with a non-toxic gas that is substantially free of $CO_2$. The alcohol system is therefore advantageous to chemical processes wherein reversibility of the solvent switching is desirable. An advantage of the water system is the rapid rate of reaction to form the bicarbonate ionic liquids from the nonionic liquids, perhaps due to a more favorable thermodynamic process. Due to this fast rate of reaction relative to the alcohol system, it is postulated that if a mixture of water and alcohol is used, the water will be used up prior to the consumption of the alcohol. This selectivity may have applications in industry in processes where it is desirable to remove water from solvents or other liquids. If the quantity of reactant was known, this method may be useful for removing water from alcohols as well. Similarly, consumption of alcohol in a solvent mixture to form a nonionic liquid as described may be desirable.

Compounds of the invention may have higher aliphatic ($C_5$-$C_{20}$) and/or siloxyl groups, however, higher aliphatic groups may cause a compound to be waxy and non-liquid at room temperature. Preferred embodiments of the invention are liquid at room temperature. Also, as the length of an aliphatic and/or siloxyl group increases, the gap between the polarities of the solvent in its two states is diminished. For these reasons, preferred aliphatic and/or siloxyl chain length is 1 to 6. A siloxyl group contains $\{-Si(R^6)_2-O-\}$ units, where $R^6$ is preferably a substituted or unsubstituted alkyl, aryl (including heteroaryl), or alkoxy moiety. (Other possible substitutents are listed below.) Conveniently, in some discussions herein, the term "aliphatic/siloxyl" is used as shorthand to encompass aliphatic, siloxyl, and a chain which is a combination of hydrocarbon and siloxyl units. A compound having a group that includes an ether or ester moiety is also encompassed by the invention. In preferred embodiments, the aliphatic/siloxyl group is alkyl. Aliphatic/siloxyl groups may be substituted with one or more moieties such as, for example, a substituent is independently alkyl, alkenyl, alkynyl, aryl, aryl halide, heteroaryl, non-aromatic rings, $Si(alkyl)_3$, $Si(alkoxy)_3$, halo, alkoxy, amino, ester, amide, thioether, alkylcarbonate, phosphine, thioester, or a combination thereof. Reactive substituents such as alkyl halide, carboxylic acid, anhydride, aldehyde and acyl chloride are not preferred.

In other embodiments of the invention all of the $R^{1-5}$ groups of the compounds of the invention are not higher aliphatic/siloxyl; they are lower aliphatic/silyl groups, and are preferably small, nonpolar and non-reactive. Examples of such groups include lower alkyl ($C_1$ to $C_4$) groups. Preferred examples of the lower aliphatic/silyl groups are $CH_3$, $CH_2CH_3$, $CH(CH_3)_2$, $C(CH_3)_3$, $Si(CH_3)_3$, and phenyl. Monocyclic, or bicyclic ring structures, such as, for example, DBU, are also preferred.

In certain embodiments, the amidine or guanidine does not have any N—H bonds. In preferred embodiments, conversion of the liquid mixture to an ionic liquid is complete. In certain embodiments, the conversion to ionic liquid is not complete; however, a sufficient amount of the liquid mixture is converted to the ionic liquid form to change the properties of the liquid. Analogously, in some embodiments, the conversion of ionic liquid back to the nonionic liquid may not be complete; however a sufficient amount of the ionic liquid is converted to the nonionic liquid mixture to cause a useful change in the properties of the liquid.

In other embodiments, an amidine moiety (or guanidine moiety or other nitrogen-containing organic moiety) is present within the same molecule as an alcohol moiety, such that the molecule converts into a zwitterionic species in the presence of $CO_2$. Preferably, the zwitterionic form of the compound converts back to its uncharged form when the $CO_2$ is removed. A chemical scheme depicting the formation of a zwitterionic ionic liquid is depicted below, where B represents an organic basic moiety such as amidine or guanidine and where the curved line represents portions of the molecule between the basic moiety and the alcohol moiety.

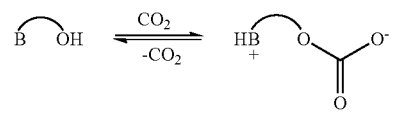

It should be understood that the invention further encompasses a combination of amidines, a combination of guanidines, and a combination of amidines and guanidines that react to form ionic liquids in the presence of water or alcohol, or a combination thereof, and in the presence of $CO_2$, $CS_2$, COS, or a combination thereof, as discussed herein. Similarly, a combination of nitrogen-containing organic compounds, with or without amidines, guanidines or amines, are also included in the invention.

Preferably, the choice of alcohol should complement the amidine or guanidine being used in each system. Alcohols that were tested in a system of DBU and $CO_2$ were 1-propanol, 1-butanol, 1-hexanol, 1-octanol, 2-octanol, 1-decanol, and phenol (see Example 1). Certain of these systems (e.g., 1-propanol, 1-butanol, phenol) formed viscous ionic liquids at room temperature. Miscibility data for the ionic liquids with traditional nonpolar solvents is presented in Table 1. The ionic liquids were thoroughly characterized spectroscopically by NMR and the NMR data is presented in Tables 2 and 4. Analogous data for unreacted alcohols is presented in Tables 3 and 5 for ease of comparison. Results of conductivity studies of neat DBU/1-hexanol and neat DBU/1-tert-butanol during $CO_2$ bubbling are presented in FIGS. 12A and 12B. The ionic liquids prepared from 1-hexanol, 1-octanol and 1-decanol appeared liquid at room temperature upon preparation. However, subsequent melting point tests (by freezing and thawing samples) showed their melting points to be slightly above room temperature (see FIG. 3). In contrast, the salts prepared by the reaction of $CO_2$ with an equimolar mixture of DBU and water (Perez, 2004; Hon et al., 1986; Heldebrant et al., 2005), DBU and methanol (Main, 2001;

Munshi, 2002) and DBU and ethanol were reported to have formed white solids at room temperature ($T_{dec}$ was 104-108° C. for bicarbonate). In addition, 3-ethyl-3-pentanol, a tertiary alcohol, did not react with $CO_2$ and DBU, either in neat form or in $CDCl_3$.

Exposure of a 1:1 mixture of the two miscible nonionic liquids, DBU and 1-hexanol, to gaseous $CO_2$, at 1 atmosphere, caused a conversion to an ionic liquid having a melting temperature slightly above room temperature (see FIG. 1 for the chemical scheme and Example 1 for procedural details). This exothermic reaction caused a marked increase in the viscosity of the resultant liquid. NMR data for the n-hexanol/DBU system is presented in Table 6. The detection of the hexylcarbonate anion was confirmed by mass spectroscopy as described in Example 1A. The ionic liquid was converted back into a nonionic liquid by bubbling argon through the liquid at room temperature. The same reaction was also performed at 50° C.; it occurred more rapidly at the higher temperature.

Conversion between a nonionic liquid and an ionic liquid results in a change in the properties of the solvent. As depicted in FIG. 4, the nonionic liquid mixture of 1-hexanol and DBU under $N_2$ was miscible with decane, which is a nonpolar solvent. The ionic liquid that was formed from 1-hexanol/DBU/$CO_2$ was immiscible with decane (see Table 1). Thus $CO_2$ and $N_2$ at 1 bar can be used as triggers of immiscibility and miscibility, respectively. Equimolar mixtures of DBU with 1-butanol, 1-hexanol and 1-octanol exhibited the same behaviour with hexane as was described above for decane. The nonionic forms (while under $N_2$) were miscible. The ionic forms (while under $CO_2$) were immiscible. However, miscibility was restored when $N_2$ was bubbled through the mixtures. By contrast, a 1:1 mixture of DBU and 1-decanol was miscible with hexane even when exposed to $CO_2$. In this case, the relatively low polarity of the ionic form, due to the length of the decyl chain in the alcohol, caused the ionic form to be sufficiently nonpolar so as to be miscible with hexane.

Switchable solvents are useful for extraction of a solute from a mixture, a solution, or a matrix. After extraction, the switchable solvent is triggered to switch to its other form, to cause the precipitation or separation of the solute from the solvent. The solvent could then be re-used. Solutes for extraction are either pure compounds or mixtures of compounds. They include both contaminants and desired materials. Such solutes can be extracted from various compositions, including, without limitation, soil, clothes, rock, biological material (for example, wood, pulp, paper, beans, seeds, meat, fat, bark, grass, crops, fur, natural fibres, cornstalks, oils), water, equipment, or manufactured materials (for example, machined parts, molded parts, extruded material, chemical products, refined oils, refined fuels, fabrics, fibres, sheets, and like materials, whether made of metal, mineral, plastic, inorganic, organic, or natural materials or combinations thereof). Desired solutes to be extracted include, without limitation, medicinal compounds, organic compounds, intermediate compounds, minerals, synthetic reagents, oils, sugars, foods, flavorants, fragrances, dyes, pesticides, fungicides, fuels, spices, and like materials.

Studies were conducted on the effect of polarity on solubility of solid solutes in ionic and nonionic forms of a DBU/1-propanol mixture. For solid solutes, 50 mg of solute were added to 2.22 mL of switchable solvent mixture. The mixtures were then hand shaken and solubility was determined qualitatively. Results are presented in Tables 14 and 15 and indicate that switchable solvents are particularly suitable for separation of solutes such as, for example, decane, tetracosane, polystyrene, stilbene, glucose and [$PhCH_2NEt_3$]Cl, since these substances were soluble or miscible in one of the ionic or nonionic forms but not in the other form. Solutes that could react with either amidine or alcohol are not suitable for dissolution in amidine/alcohol mixtures; such solutes may be, for example, acids, strong bases and alkyl halides.

A study of the suitability of switchable solvents for use as a medium in which to synthesize polymer was conducted using styrene. Details are provided in Example 10. A system of DBU and 1-propanol was used in its nonionic form for synthesis of polymer and then switched to ionic form for isolation of the polymeric product. A monomer, styrene and an initiator, $K_2S_2O_8$, were added to the nonionic solvent mixture under nitrogen. The reaction was allowed to proceed and a solution of polymer was obtained. Isolating polymer from traditional solvent is difficult, since the product is typically so fine that it clogs up a filtering apparatus. In this case, when the switchable solvent was switched to its viscous ionic form and was diluted (optional) with a non reactive solvent, 1-propanol, polymer particles precipitated from solution and were easily filtered. Since switchable solvents have two distinct sets of physical properties that can be switched from one set to the other set by a trigger, they are well suited to assist with isolating solutes that are difficult to isolate using traditional solvents.

The $CO_2/N_2$ switchable system of an equimolar mixture of DBU with ethanol exhibited different behaviour from the higher alkylcarbonates discussed above. The amidinium ethylcarbonate was immiscible with hexane, toluene and ethyl acetate, and formed a separate liquid phase even though it is solid when pure. It is not yet understood whether this is supercooling behaviour or a melting point depression due to the presence of the extra solvent. The polarity of liquid [DBUH][$O_2$COEt] is far higher than that of liquid [DBUH][$O_2COC_6H_{13}$].

The polarity of the 1-hexanol/DBU 1:1 mixture was measured with the use of two solvatochromic dyes, Reichardt's dye (a pyridinium N-phenolate betaine also known as $E_T(30)$) (Reichardt, 2003) and Nile Red. Reichardt's dye was green when dissolved in the alcohol/DBU mixtures under $N_2$ and appeared yellow when dissolved in the same liquids under $CO_2$. This colour change is likely due at least partly to protonation of the dye or hydrogen-bonding of the dye with the acidic proton of protonated DBU or carbonic acid monohexylester; for this reason use of Reichardt's dye was discontinued in this study.

Ionic solvents were made from reacting DBU and C3 to C10 alcohols with carbon dioxide. The polarities of the resultant ionic liquids are represented by the wavelength of maximum absorbance of light of Nile Red dissolved in the ionic liquids presented in FIG. 2 (upper curve). Similarly, the polarities of the equimolar DBU/alcohol mixtures under $N_2$ are represented by the lower line in FIG. 2.

The melting point of the DBU/alcohol/$CO_2$ ionic liquids as a function of the alcohol's chain length are depicted graphically in FIG. 3. This graph shows that for room temperature applications of the switchable solvent of the invention, a carbon chain length of 3 to 6 is preferred to avoid freezing of the ionic liquid. A carbon chain length of 3 to 5 is particularly preferred for this reason. It is noted that a pure ionic liquid of carbon length of 6 is prone to freeze at approximately 22° C.

The switchable solvents that use water rather than alcohol as the second component of the nonionic form differ from the switchable solvents that use alcohol because the amidines, guanidines or other N-containing organic bases are usually but not necessarily immiscible with water. Thus in most cases the nonionic form of a base/water mixture would consist of two phases, one organic and one aqueous, and would merge to a single ionic liquid phase upon exposure to $CO_2$. If the melting point of the bicarbonate salt thus produced is above room temperature, and a lower melting point is desired, then the molar ratio of water to base in the original mixture is preferably greater than 1 or less than 1. This miscibility behaviour is observed in the systems described in the N,N,N',N'-tetramethyl-N"-phenylguanidine and N,N,N',N'-tetramethyl-N"-(2-fluorophenyl)guanidine schemes of FIG. 5. In contrast, most base/alcohol pairs and some base/water pairs form miscible mixtures even in their nonionic forms.

The particular choice of alcohol for use with the invention depends on the amidine or guanidine compound. In the case of DBU, methanol and ethanol are not preferred when it is desired to obtain a liquid at room temperature. In contrast, propanol or a higher alcohol are suitable for DBU.

In certain embodiments of the invention, a combination of two or more alcohols is used in place of a single alcohol. In some embodiments it may be preferably to have multicomponent mixtures to decrease the melting point of the resultant ionic liquid and/or modify other properties of the ionic or nonionic forms of the switchable solvent. In some embodiments of the invention, ionic liquids or nonionic liquid mixtures are added to conventional solvent(s) in either form. Advantages of adding conventional solvents to switchable solvents include increased speed of switching, less viscous mixtures and maintenance of conductivity. A study comparing the conductivity of DBU and 1-propanol versus DBU, 1-propanol and tetrahydrofuran is presented in FIG. 13. Results of a conductivity study of DBU, 1-hexanol and toluene are shown in FIGS. 14A and 14B.

In some embodiments, the ratio of non-gaseous reactants (amidine or guanidine or similar base and alcohol, water or alcohol/water mixture) is about equimolar. This is advantageous since when the ionic liquid is prepared from this mixture, there will remain little or no unreacted reactant(s) and the change in physical properties upon switching will be maximized.

In other embodiments, the ratio of non-gaseous reactants is not equimolar. As a result, when the ionic liquid is formed, it is present with a reactant. This situation may be advantageous, for example it may lower the melting point.

In other embodiments, carbon dioxide may be replaced by substitute gases carbon disulfide ($CS_2$) or carbonyl sulfide (COS). Carbonyl sulfide is not preferred because of its flammability, its negative impact on human health (irritant, damage to nervous system), and its negative impact on the environment. Carbon disulfide is not preferred because of its flammability, its toxicity, and its negative impact on the environment. Nevertheless, $CS_2$ and COS are expected to be capable of triggering the same change in the switchable solvents as can $CO_2$.

Carbon dioxide may be provided from any convenient source, for example, a vessel of compressed $CO_2(g)$ or as a product of a non-interfering chemical reaction. The ionic liquid can be converted to a nonionic liquid by removing the carbon dioxide, for example, by exposing the mixture to a gas that contains insufficient $CO_2$ to sustain the ionic form, e.g., a gas that contains substantially no carbon dioxide. Preferably, the gas is non-toxic. Preferred gases that are substantially free of $CO_2$ include, for example, argon, $N_2$, argon, air that has insufficient carbon dioxide to switch the nonionic liquid mixture to ionic liquid, and air with the carbon dioxide component removed. In some embodiments, dried air, without any removal of the existing $CO_2$ content, will suffice. In some cases, normal air, without any removal of either the existing $CO_2$ or the $H_2O$ content, will suffice. Conveniently, such exposure is achieved by bubbling the gas through the mixture or by any other means of providing efficient contact between the liquid and gas phases. However, it is important to recognize that heating the mixture is an alternative method of driving off the $CO_2$, and this method of converting the ionic liquid to nonionic liquid is also encompassed by the invention. In certain situations, especially if speed is desired, both bubbling (or other means of providing efficient contact) and heat can be employed. Heat may be supplied from an external heat source, preheated nonreactive gas, exothermic dissolution of gas in the liquid phase, or an exothermic process or reaction occurring inside the liquid.

Some embodiments of the invention require a pressure of $CO_2$ greater than 1 bar to switch the solvent from nonionic to ionic. Preferred embodiments are able to react with $CO_2$ at 1 bar or less to trigger the switch. High pressure switchable solvents require a pressure of $CO_2$ greater than 1 atm to switch to ionic form and are substantially completely switched to the nonionic form by a decrease in $CO_2$ pressure to about 1 atm. High pressure switchable solvents may be more time efficient than atmospheric-pressure systems. These high pressure switchable solvents may differ from the atmospheric-pressure switchable solvents by a change in the steric or electronic properties of the amine base (e.g., guanidine or amidine). Such molecules may include, for example, tertiary amines, such as N-methylpyrrolidine, and amidines and guanidines with decreased basicity when compared to DBU such as amidines and guanidines having aryl groups directly attached to one or more of the N atoms. Alternatively, high pressure switchable solvents may differ from the atmospheric pressure switchable solvents by a change in the steric or electronic properties of the alcohol. It should be understood that the invention encompasses amidine or guanidine compounds that have lower or about equal basicities than DBU and that react with $CO_2$ in the presence of alcohol, water or a combination thereof under high pressure (i.e., are high pressure switchable solvent compounds).

1-methylpyrrolidine and 1-pentanol were tested at high pressure $CO_2$; a decrease in polarity from 526 nm to 511 nm was observed at 57 bar $CO_2$. DBU and 2-butanol were studied at high pressure $CO_2$; an increased viscosity and slightly lowered polarity were observed relative to low pressure $CO_2$. DBU and 2-propanol were studied at high pressure $CO_2$; an increased polarity (546 nm) was observed relative to low pressure $CO_2$ (541 nm).

Although the requirement for high pressure in generation of an ionic liquid can be viewed as a disadvantage, the ability to switch the properties of such a molecule rapidly by reduction of the $CO_2$ pressure may conversely be viewed as an advantage. For these reasons, the high pressure switchable solvents may be particularly suited to some industrial processes, for example, where elevated pressures are already used or where rapid solvent switching is required.

Atmospheric pressure switchable solvents include amidines, guanidines and primary and secondary amines, each with aliphatic/siloxyl portion(s) as discussed below. If the switch to the ionic form is to be easily reversible, the amidines or guanidines are preferably peralkylated. The term "peralkylated" as used herein means that the amidine or guanidine has alkyl or other groups connected to the N atoms so that the neutral molecule contains no N—H bonds. This lack of N—H groups is intended to avoid potentially irreversible reactions with carbon dioxide. If the switch to the ionic form is not to be reversible, then there is no preference that the amidine or guanidine be "peralkylated".

An alternative method of preparing a high-pressure switchable solvent would be to use an alcohol that shows diminished conversion to the alkyl carbonate (in the presence of an amidine or guanidine and carbon dioxide) at 1 atm of $CO_2$ pressure. An example of such an alcohol is a secondary or tertiary alcohol.

An advantage of switchable solvents is that they facilitate organic syntheses and separations by eliminating the need to remove and replace solvents after each reaction or separation step, e.g., when a solvent with different physical properties is needed. With triggers that are capable of causing a drastic change in the solvent properties while it is still in the reaction vessel, it may be possible to use the same solvent for two or more consecutive reaction or separation steps. This would eliminate the need to remove and replace the solvent.

Reuse and recycling of solvents of the invention are convenient, with attendant economic benefits. The time required to switch between the ionic and nonionic forms according to the invention is short. In certain applications, it may be advantageous to convert from nonionic to ionic and then back again (or vice-versa). For example, the solvent could be made nonionic to be miscible with a nonpolar liquid, and then the solvent could be switched to its ionic form to allow for separation of the resulting two liquid components. The liquid components may or may not appear as distinct layers. Separation of the components may include decanting, or centrifuging. After separation, it may be desirable to convert the ionic form back to its nonionic form. Thus the solvent can be reused. In some embodiments it may be desirable to use the solvent in its ionic form. This molten salt form would separate from aqueous solutions when converted to its nonionic form, allowing for easy recovery and reuse of the solvent.

The invention provides a convenient system to controlling the properties of a solvent. Thus, it is useful in many industrial applications. For example, a chemical reaction that requires a polar solvent could be performed in the switchable solvent while in its ionic form. Once the reaction is complete, the solvent could be switched to its nonionic form which is substantially incapable of dissolving the product of the reaction. This would force the product to precipitate, if solid, or become immiscible, if liquid. The solvent could then be separated from the product by physical means such as, for example, filtration or decantation. If appropriate, the solvent could then be switched back to its ionic form and reused. This method allows the use of a polar solvent without the requirement for an energy-intensive distillation step to remove the solvent. Such distillation steps are costly since many polar solvents have high boiling temperatures.

A switchable solvent would be advantageous in a two-step chemical synthesis in which the first step requires a polar solvent and the second step requires a nonpolar solvent (or vice versa). The first chemical reaction, which requires a polar solvent, could be performed in the solvent while in its ionic form, producing a chemical intermediate. Once the first reaction is complete, the solvent could be switched to its nonionic form, which is capable of maintaining the chemical intermediate in solution. The intermediate would then be converted to a desired product by a second reaction, which requires a nonpolar solvent. Traditionally, this two-step synthesis would be performed using two solvents, a polar solvent for the first step, and a nonpolar solvent for the second step. The removal of the polar solvent after the end of the first step would involve extra cost, time and energy. Thus switchable solvents as described herein can lessen the financial and environmental costs of industrial processes, by saving time and energy normally expended during solvent substitutions, or during solvent removal from product or solute.

Switchable solvents of the invention can be useful in water/solvent or alcohol/solvent separations in biphasic chemical reactions. As seen in FIG. 4, separation of a nonionic liquid from a switchable solvent may be effected by switching the switchable solvent to its ionic form. This ability to separate a liquid from a solvent may be useful in many industrial processes where upon completion of a reaction, one of the solvents is switched to its ionic form allowing for facile separation of the two distinct phases. Thus a switchable solvent, may be used in its nonionic state as a medium for a chemical reaction. Upon completion of the reaction, the chemical product is readily separated from solution by switching the solvent to its ionic form. The solvent can then be recovered and reused, if appropriate.

A further aspect of the invention is a nonionic liquid mixture that is largely nonconductive (or only weakly conductive) of electricity, that becomes more conductive when it is converted to its ionic form, and that this change may be reversible. In the hexanol/DBU system described in Example 1A, conductivity of the ionic form was 20 times that of the nonionic form. A similar result can be seen in FIG. 10 for a guanidine system. Such a conductivity difference would enable the liquid to serve as an electrical switch, as a switchable medium, as a detector of $CO_2$, $CS_2$ or COS, or as a sensor of the presence of $CO_2$, $CS_2$ or COS. This ability of the ionic liquid to conduct electricity can have applications in electrochemistry, in liquid switches and in sensors and/or detectors. Common, affordable $CO_2$ sensors are typically effective at 2-5% $CO_2$. $CO_2$ sensors that work between 2-100% are usually large and prohibitively expensive. A chemical approach based on switchable solvents can cost much less.

Preliminary studies were conducted on use of the change in conductivity of DBU/ROH mixtures and of secondary amines for sensing $CO_2$ content of gas mixtures. These studies are described in Examples 7 and 8. In both systems, inert solvent can be added for greater signal and faster response. See FIGS. 13 and 14 for studies comparing neat systems to systems with added inert solvents such as THF and toluene. In the secondary amine system the solvent is preferably polar (e.g., DMSO or MeCN), rather than nonpolar (e.g., toluene).

Conveniently, a $CO_2$ sensor based on conductivity changes of a reversibly switchable solvent as described herein is effective in the range of about 5 to about 15% $CO_2$. For example, a thin film of neat DBU/1-hexanol (or other suitable amidine and/or guanidine/alcohol) can be used as a $CO_2$ sensor. The thin film allows for a shortened amount of time for switching compared to the amount of time shown in FIG. 12 for switching of a larger quantity of neat DBU/1-hexanol. Alternatively, mixing the amidine and/or guanidine/alcohol mixture with an inert solvent would shorten the amount of time for switching, as seen in FIG. 13.

WORKING EXAMPLES

DBU (Aldrich, Oakville, Ontario, Canada, 98% grade) was dried by refluxing over $CaH_2$ and distilled under reduced pressure onto 4 Å molecular sieves and then deoxygenated by repeated freeze/vacuum/thaw cycles or by bubbling with carbon dioxide followed by filtration to remove any bicarbonate precipitate. Alcohols (99+%, anhydrous) were used as received from Aldrich. Decane (Aldrich, 99+% grade) was degassed with nitrogen prior to use. Hexanes (Fisher Scientific, HPLC grade) and toluene (Fisher Scientific, HPLC grade) were degassed and dried by passing them through an activated alumina column under nitrogen prior to use. Ethyl acetate (Fisher Scientific, HPLC grade) was degassed with nitrogen prior to use. Supercritical grade $CO_2$ (99.999%, $H_2O$<0.5 ppm), nitrogen (99.998%, $H_2O$<3 ppm) and argon (99.998%, $H_2O$<5 ppm) were used as received from Praxair Canada Inc., (Mississauga, Ontario, Canada).

Example 1

Reversible Solvent Switching in an Amidine and Alcohol System

Example 1A

Reversible Solvent Switching in a DBU and 1-Hexanol System

Dried DBU (0.60 mL, 4.0 mmol, see FIG. 1) and 1-hexanol (0.50 mL, 4.0 mmol) were placed in a dry glass NMR (Nuclear Magnetic Resonance) tube in a glove box (Vacuum Atmospheres Company, Hawthorne, Calif.) under $N_2$. Carbon dioxide was bubbled through the liquid via a hollow narrow-gauge stainless steel tube which was inserted in the solution within the NMR tube. The rate of bubbling was 2 bubbles per second for 1 hour. The liquid became increasingly viscous. The conductivity of a similar solution was measured using an immersible conductivity probe (Jenway, model 4071, available at Canadawide Scientific, Ottawa, Canada); it increased more than 20 fold. The $^1H$ NMR spectrum of the resultant solution, although broadened due to the solution's viscosity, clearly indicated complete conversion to [DBUH][$O_2CO(CH_2)_5CH_3$] (where "DBUH" is protonated DBU) with no residual signals for free 1-hexanol or unprotonated DBU. The $^1H$ NMR resonance in $CDCl_3$ attributed to the oxygen-bound methylene of the hexyl group had shifted to 3.90 ppm from 3.58 ppm (the resonance for the same methylene group in unreacted hexanol). This resonance is comparable to the corresponding chemical shifts seen for $CH_3C(O)O(CH_2)_5CH_3$ (in $CDCl_3$) at 4.05 ppm (Reynders, 1990) and dihexyl carbonate at 4.13 ppm (in $CCl_4$) (Sakai, 1971).

Please see the picture below for the numbering scheme for positions in the DBU structure.

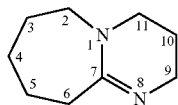

Spectroscopic Data for [DBUH][$O_2CO(CH_2)_5CH_3$]:
$^1H$ NMR (δ, ppm, in $CDCl_3$) 3.90 (t, 2H, hexyl C1), 3.49 (m, 4H, DBUH C2 and C11), 3.43 (t, 2H, DBUH C9), 2.81 (br, 2H, DBUH C6), 2.00 (quintet, 2H, DBUH C10), 1.75 (br, 6H, DBUH C3, C4, and C5), 1.58 (quintet, 2H, hexyl C2), 1.37 (m, 2H, hexyl C3), 1.29 (br, 4H, hexyl C4 and C5), 0.87 (t, 3H, hexyl C6).
$^{13}C\{^1H\}$ NMR (δ, ppm, in $CDCl_3$, referenced to $CDCl_3$ at 77.2 ppm) 164.9 (DBUH C7), 158.7 ($O_2COR$), 64.6 (hexyl C1), 53.5 (DBUH C2), 48.1 (DBUH C11), 38.6 (DBUH C9), 32.3 (DBUH C6), 31.5 (hexyl C4), 29.4 (hexyl C2); 28.8 (DBUH C4), 26.8 (DBUH C3), 25.5 (hexyl C3), 24.0 (DBUH C5), 22.2 (hexyl C5), 19.7 (DBUH C10), 13.7 (hexyl C6).
IR (neat) 2938 (m), 1648 (s), 1613 (s), 832 (m), 688 $cm^{-1}$ (m).
Mass Spectroscopy of a Mass Spectroscopy Sample in Electrospray Ionization negative mode ("MS/MS (ESI, negative mode)" 145.1 (M), 101.1 (M-$CO_2$), 99.1 (M-$H_2CO_2$), 83.0 (M-$H_2CO_3$), 60.0 ($CO_3$), where "M" is the anion $C_6H_{13}OCO_2^-$.

For comparison, literature shows that [$NBu_4$][$O_2COEt$] has a $^{13}C\{^1H\}$ NMR signal for the carbonyl at 157.9 ppm in $CDCl_3$ and IR peaks at 2940, 2880 and 1670 $cm^{-1}$ in KBr (Verdecchia, 2002).

Spectroscopic changes upon exposure of the hexanol/DBU mixture to $CO_2$ are presented in Tables 2, 4 and 6. Solvatochromic data measuring the polarity of the liquid before and after exposure to $CO_2$ are presented in FIG. 2.

Reversability of the reaction was confirmed when a sample of the ionic liquid in an NMR tube was heated to 50° C. and argon was bubbled through the sample for 1 h. The viscosity dropped greatly. The $^1H$ NMR spectrum after this procedure was consistent with the spectra of 1-hexanol and DBU, showing no peaks for residual ionic liquid.

Exposure of [DBUH][$O_2COC_6H_{13}$] ionic liquid to moist air resulted in the appearance of a white solid within a few minutes. The white solid, washed with acetonitrile, was identified as the bicarbonate salt [DBUH][$O_2COH$] by IR and $^1H$ NMR (in $CDCl_3$).

Example 1B

Reversible Solvent Switching in Systems of DBU and Various Alcohols

Analogous tests as the one described in Example 1A were performed for DBU and n-chain alcohols having 1, 2, 3, 4, 6, 8 and 10 carbon atoms. The products of the DBU with the C3-C10 alcohols were liquids at room temperature as indicated in FIG. 3. Preliminary tests of DBU with secondary and tertiary alcohols were not successful in obtaining complete conversion to ionic liquids. An example of a tertiary alcohol, 3-ethyl-3-pentanol, with an equimolar amount of DBU did not react with carbon dioxide. Secondary alcohols (2-octanol, (1R,2S,5R)-(-)-menthol and (1S)-endo-(-) borneol) reacted to form an ionic liquid, but complete conversion was not obtained. The greatest conversion of these-secondary alcohols (about 64%) was obtained with 2-octanol.

In the cases of the primary n-alcohols, the ionic liquids were characterized by $^1H$ and $^{13}C$ NMR spectroscopy. The reversibility of the reaction in each case to reform DBU and the appropriate alcohol was also confirmed by $^1H$ NMR. Spectroscopic changes upon exposure of the alcohol/DBU mixtures to $CO_2$ are presented in Tables 2, and 4 while the unreacted alcohols' spectroscopic data is presented in Tables 3 and 5, for comparison purposes.

Solvatochromic data measuring the relative polarities of the DBU/alcohol mixtures before exposure to $CO_2$ and the corresponding ionic liquids after exposure to $CO_2$ are presented graphically in FIG. 2, where the y axis is the wavelength of the peak of Nile Red dye in the solvent. High polarity is represented by a greater wavelength value, and lower polarity is represented by a lower wavelength value.

The melting point of the ionic form of the switchable solvent made from DBU and an alcohol having 1 to 10 carbon atoms is presented graphically in FIG. 3 wherein the y axis is the melting point and the x axis is the length of carbon chain of the R component of the salt which is derived from the alcohol.

Example 2

Miscibility Switching in a DBU and Alcohol System

In an inert atmosphere, 26.8 mmol each of DBU (95 ppm $H_2O$) and 1-hexanol (26 ppm $H_2O$) were charged into a flame-dried flask. N-Decane (2 mL, undried) was added and was found to be miscible at room temperature; only one homogeneous liquid phase was observed. $CO_2$ ($H_2O$<5 ppm) was slowly bubbled through the decane/1-hexanol/DBU mixture at 1 bar overnight. The resultant mixture appeared split into two separate liquids. Argon was then bubbled through the two-phase liquid mixture for 1 h at 35° C. After 1 h, the two liquids had merged into one liquid. A schematic representation of this reversible reaction appears in FIG. 4. Similar experiments were performed with hexane in place of decane and with several alcohols (1-propanol, 1-butanol, 1-hexanol, 1-octanol, and 1-decanol) in place of 1-hexanol; similar results were obtained except that with 1-decanol, no phase split was observed even after the treatment with $CO_2$. Miscibility data for alcohol/DBU systems is presented in Table 1.

Example 3

Guanidine and Water Systems

Example 3A

Solvent Switching in N,N,N',N'-tetramethyl-N"-phenylguanidine Guanidine and Water Systems An ionic liquid was reversibly formed by bubbling carbon dioxide through a solution of N,N,N',N'-tetramethyl-N"-phenylguanidine (500 mg) (see FIG. 5A) in wet diethyl ether (5 mL). The liquid bicarbonate salt formed a separate liquid phase from the diethyl ether (see FIG. 5C). The ionic liquid was characterized by $^1$H NMR spectroscopy wherein the proton resonances of the guanidinium bicarbonate had shifted relative to the corresponding resonances of the unreacted N,N,N',N'-tetramethyl-N"-phenylguanidine (see FIG. 7).

Similarly, an ionic liquid was formed by bubbling carbon dioxide through a solution of N,N,N',N'-tetramethyl-N"-(2-fluorophenyl)guanidine (500 mg) (see FIG. 5B) dissolved in wet diethyl ether (5 mL). The liquid bicarbonate salt formed a separate liquid phase that was distinct from the diethyl ether as depicted in FIG. 5. The ionic liquid was characterized by $^1$H NMR spectroscopy wherein the proton resonances of the guanidinium bicarbonate had shifted relative to the corresponding resonances of the unreacted N,N,N',N'-tetramethyl-N"-(2-fluorophenyl)guanidine.

An ionic liquid was formed, in the absence of ether, by bubbling carbon dioxide through an equimolar mixture of water and N,N,N',N'-tetramethyl-N"-phenylguanidine. Prior to bubbling, the liquids appear as a biphasic mixture with the guanidine on the top and the water on the bottom. After bubbling, the liquid appeared as a single phase ionic liquid.

Attempts to reverse the switch to reform the nonionic guanidines of Example 3 by bubbling the ionic liquids with argon have been unsuccessful to date.

Example 3B

Solvent Switching for N-phenyl-N',N',N",N"-tetramethylguanidine (PhTMG) and Water PhTMG (2 mL) and water (2 mL) were placed together in a small vial, forming a two-phase mixture. $CO_2$ was bubbled through the mixture for 2 h, giving a single colourless viscous liquid phase, believed to be a mixture of [PhTMGH][$O_2$COH] and water. $^1$H and $^{13}$C NMR spectra of this liquid in $CD_3OD$ and that of the HCl salt of PhTMG in the same solvent matched, as seen below.

Characterization of the viscous liquid: $^1$H NMR ($CD_3OD$) 3.0 (s, 12H, Me), 7.1 (d, 2H, ortho), 7.2 (t, 1H, para), 7.4 ppm (t, 2H, meta). $^{13}$C NMR ($CD_3OD$) 39.9 (Me), 121.3 (ortho), 125.7 (para), 130.3 (meta), 138.8 (N—C(arom)), 159.5 (N═C), 160.6 ppm ($O_2$COH).

PhTMG.HCl: $^1$H NMR ($CD_3OD$) 3.0 (s, 12H, Me), 7.1 (d, 2H, ortho), 7.2 (t, 1H, para), 7.5 ppm (t, 2H, meta). $^{13}$C NMR ($CD_3OD$) 40.8 (Me), 122.7 (ortho), 127.3 (para), 131.8 (meta), 139.8 (N—C (arom)), 160.5 (N═C).

Example 4

Studies of Guanidine and Alcohol Systems

Example 4A

Reversible Solvent Switching in Me-MTBD Guanidine and Alcohol System

An ionic liquid was reversibly formed by bubbling carbon dioxide through a mixture of 1,3,4,6,7,8-hexahydro-1-methyl-2H-pyrimido[1,2-a]pyrimidine ("Me-MTBD", see FIG. 6A), which was used as purchased from Aldrich, and 1-octanol. The formation of the ionic liquid was confirmed by $^1$H NMR spectroscopy. The same reaction with methanol in place of octanol gave a solid product. Attempts to reverse the switch to reform Me-MTBD and 1-octanol by heating the ionic liquids have been unsuccessful to date.

An ionic liquid was reversibly formed (as described in Example 1A) by bubbling carbon dioxide through a solution of N,N,N',N'-tetramethyl-N"-butylguanidine (see Example 5 and FIG. 6B) and methanol. The formation of the ionic liquid was confirmed by $^1$H and $^{13}$C NMR spectroscopy, including the $^{13}$C NMR technique known as "attached proton test" (APT or DEPT). The reversibility of the reaction to reform the nonionic guanidine and methanol was confirmed by $^1$H and $^{13}$C NMR. The reversal was achieved by bubbling $N_2$ through the neat ionic liquid at 50° C. The reversal was also achieved by dissolving the ionic liquid in a solvent and then bubbling $N_2$ through that solution. The reversal by the latter method, at room temperature, took 12 hours of bubbling in DMSO and greater than 24 hours in $CDCl_3$.

Example 4B

Reversible Solvent Switching in 2-butyl-1,1,3,3-tetramethylguanidine and Alcohol System A reversibly switchable room temperature ionic liquid was formed by exposing an equimolar mixture of 2-butyl-1,1,3,3-tetramethylguanidine (Schuchardt et al. 1995; Cost et al. 1998) and methanol to gaseous $CO_2$ at one atmosphere. Reversibility of this system was demonstrated by $^1$H and $^{13}$C NMR spectroscopy and conductivity studies (see FIGS. 9A-C, and 10). Formation of the ionic liquid occurred after bubbling $CO_2$ for 20 minutes through a 1:1 molar ratio mixture of 2-butyl-1,1,3,3-tetramethylguanidine and methanol. The ionic liquid was then converted back to 2-butyl-1,1,3,3-tetramethylguanidine and methanol by bubbling the mixyure with $N_2$ or argon overnight. The ionic liquid can also be reversed solely by heat, as indicated by a thermogravimetric study (see FIG. 11 in which the ionic liquid underwent reversal, releasing $CO_2$ and low-boiling methanol at temperatures as low as 50° C.).

FIG. 9A shows an NMR spectrum of the initial equimolar solution of 2-butyl-1,1,3,3-tetramethylguanidine and methanol. Upon the addition of $CO_2$, protonation of the guanidine and formation of the methyl carbonate anion took place. This is evidenced in $^1$H NMR by an upfield shift in the aliphatic protons, and the collapse of the two N-Me peaks into one peak (see FIG. 9B). Finally, FIG. 9C shows the $^1$H NMR after nitrogen bubbling for 16 hours. The ionic liquid has indeed reversed to its original components.

$^{13}$C NMR spectra exhibited the appearance of a characteristic carbonate peak at 161 ppm. Chemical shifts in the methoxyl and aliphatic carbons, and changes in N-Me peaks were clearly observed. Unreacted $CO_2$ was not detected by $^{13}$C NMR as no peaks were present at 120 ppm.

Example 4C

Conductivity Measurement of Methanol and 2-butyl-1,1,3,3-tetramethylguanidine

The reversibility and repeatability of the conversion of an equimolar mixture of methanol and 2-butyl-1,1,3,3-tetramethylguanidine in chloroform to 2-butyl-1,1,3,3-tetramethylguanidinium methylcarbonate were confirmed by a conductivity study. This study was conducted using a JENWAY conductivity meter 4071 (Jenway, Barloworld Scientific Ltd, Essex, England). When carbon dioxide was bubbled through the guanidine and alcohol mixture, the mixture changed from non-conducting (0-10 µS/cm) to conducting (approximately 250 µS/cm) (see FIG. 10), indicating the formation of the ionic liquid 2-butyl-1,1,3,3-tetramethylguanidinium methylcarbonate. The conductivity was then switched off by applying heat (80° C.) indicating the (re)formation of methanol and 2-butyl-1,1,3,3-tetramethylguanidine. This cycle was repeated three times obtaining similar levels of conductivity each time.

Example 5

Thermogravimetric Analysis of 2-butyl-1,1,3,3-tetramethylguanidinium Methylcarbonate Thermogravimetric analysis (TGA) was used to determine the optimum temperature for driving off carbon dioxide from a sample of 2-butyl-1,1,3,3-tetramethylguanidinium methylcarbonate. The sample was heated in a TGA Q500 thermogravimetric analysis machine (TA Instruments, New Castle, Del., USA). See FIG. 11 for the resulting plot of heat flow, temperature and mass loss.

Example 6

Synthesis of N,N,N',N'-tetramethyl-N"-butylguanidine

N,N,N',N'-tetramethyl-N"-butylguanidine was prepared as follows: 9.3 g tetramethyl urea was added to 80 mL dry dichloroethane in a two-neck 250 mL round-bottom-flask. 11.3 mL oxalyl chloride was added and the solution was heated at 70*C for two hours. The solvent was evaporated in vacuo after the solution cooled to room temperature. Residual solid was then dissolved in dry acetonitrile and cooled to 0° C. 15 mL butyl amine (1.02 eq) was slowly added. The solution was slowly warmed and allowed to reflux for one hour. Finally, the mixture was cooled to room temperature and the solvent was removed in vacuo to yield 9 g of a clear oil. $^1$H(CDCl$_3$): δ (ppm): 2.99 (t, 2H); 2.62 (s, 3H); 2.53 (s, 3H); 1.39 (quintet, 2H); 1.24 (quintet, 2H); 0.78 (t, 3H). The synthesis was performed several times and the yield ranged from 37%-70%.

Example 7

Studies of DBU/Alcohol System as $CO_2$ Sensor

The following experiments were conducted to study use of a DBU/alcohol system as a $CO_2$ sensor:

(1) $CO_2$ was bubbled through an anhydrous equimolar mixture of DBU and 1-propanol at room temperature. After 30 minutes, the conductivity had risen from its initial value of 34 to values over 200 µS/cm; after further bubbling for 2 h, the value rose to 300 µS/cm.

(2) $CO_2$ was bubbled through an anhydrous THF solution containing an equimolar mixture of DBU and 1-propanol at room temperature (1:1:3 mole ratio DBU:ROH:THF). After 2 minutes, the conductivity rose from its initial value of 16 to 654 µS/cm, after which a steady drop in conductivity was observed. A loss in volume of the liquid was observed during this drop in conductivity, indicating that at least one of the components of the liquid mixture was being lost by evaporation. The rapid initial rise in conductivity indicates that the addition of an inert solvent (THF in this case) increased the rate of response of the conductivity to the presence of $CO_2$ and also increased the intensity of the signal (the magnitude of the conductivity). The inert solvent also reduced the cost of the method because THF is cheaper than DBU. The loss of liquid indicates that it would be better to use less volatile liquids.

(3) $CO_2$ was bubbled through an anhydrous toluene solution of an equimolar mixture of DBU and 1-hexanol at room temperature (1:1:3 DBU:ROH:toluene mole ratio). The conductivity rose from below the detection limit of the instrument up to a steady value of 285 µS/cm. This steady conductivity was reached after about 15 minutes. Flushing $N_2$ through the mixture at room temperature caused the conductivity to drop to 5-6 µS/cm after 75 min. Bubbling $CO_2$ through the solution again caused the conductivity to rise again, reaching a conductivity of 269-275 µS/cm after 15 min.

Results of these studies indicate that using nonvolatile components eliminates the conductivity drop seen in experiment (2); the reaction can be reversed without the use of heat, and the conductivity is reproducible.

Example 8

Studies of Secondary Amines

Example 8A

Polarity Studies of Secondary Amines

Each secondary amine (3 mL) was placed in a 1 cm glass cuvette. Nile Red, a solvatochromatic dye, was added by syringe at which time the transparent sample turned red. UV measurements were taken of this nonionic form. Each sample was then sealed with an airtight septum and bubbled with carbon dioxide from a pressurized vessel for approximately 20 minutes or until the heat of reaction subsided. UV measurements ($\lambda_{max}$) were taken again. Each sample was then switched back to nonionic form by bubbling nitrogen gas into the cuvette and heating the cuvette in a 55° C.-60° C. oil bath for up to 2.5 hours. Periodic UV measurements were taken to determine the $\lambda_{max}$. This was done until the $\lambda_{max}$ was the same as the original nonionic form. Experiments were performed twice for each amine and average values appear in Table 12.

Example 8B

Solubility and Miscibility Studies of NHEtBu

Substrate (50 mg) and ethylbutylamine (3.0 mL) were stirred together in a vial with septum under $N_2$. Whether the solid had completely dissolved was determined visually. $CO_2$ was bubbled through the solution for 30 minutes with stirring, and a visual observation of phase behaviour was conducted again. If there was a change in the phase behaviour, the vial was heated to 50° C. and $N_2$ was bubbled through the solution for 2 h to see if the change was reversible. For all cases that demonstrated a change, the change was reversible, with the exception of glucose. Glucose was insoluble before treatment with $CO_2$, soluble after $CO_2$ treatment, and remained soluble after the $N_2$ treatment. Solubility results are presented in Table 14.

The miscibility of liquids was tested in a similar manner except that the amount of the liquid substrate was 0.5 mL. Miscibility results are presented in Table 13.

Example 8C

NMR Studies of Secondary Amines

NMR spectra of carbamate salts of secondary amines in $CDCl_3$ were obtained in the following manner. Standard NMR tubes were filled to approximately 5 cm with deuterated chloroform. 2-3 drops of a secondary amine were added to the tube. An airtight septum was inserted into the top of the tube and carbon dioxide was slowly bubbled through the solution until the heat subsided. NMR results are reported in Tables 7 and 8.

Example 8D

Studies of NHEtBu System as $CO_2$ Sensor

The following experiments were conducted to study use of a NHEtBu system as a $CO_2$ sensor:

1) Neat NHEtBu at room temperature (0 μS/cm) was bubbled with $CO_2$ and had a conductivity of 0.67 μS/cm.

2) NHEtBu in MeCN (1:6 mol/mol) at room temperature had an initial conductivity of 6-12 μS/cm. $CO_2$ was bubbled through the solution for 5 min and the conductivity rose to 140 μS/cm.

3) NHEtBu in toluene (1:6 mol/mol) at room temperature had an initial conductivity of 0 μS/cm. $CO_2$ was bubbled through the solution for 30 minutes and the conductivity stayed at 0 μS/cm. Other amines (NHPrBu, NHMeBz) in toluene gave the same result.

4) NHEtBu in DMSO (1:6 mol/mol) at room temperature had an initial conductivity of 6-15 μS/cm. $CO_2$ was bubbled through the solution for 5 minutes and the conductivity rose to 500 μS/cm.

Example 9

X-Ray Crystallographic Study of [DBUH][$O_2$COMe]

A crystal of [DBUH][$O_2$COMe] (colorless, plate-shaped, size 0.35×0.25 x 0.08 mm) was mounted on a glass fiber with grease and cooled to −93° C. in a stream of nitrogen gas controlled with a Cryostream Controller 700. Data collection was performed on a Bruker SMART CCD 1000 X-ray diffractometer (Bruker BioSpin Ltd., Milton, Ontario, Canada) with graphite-monochromated Mo $K_\alpha$ radiation ($\lambda$=0.71073 Å), operating at 50 kV and 30 mA over 2θ ranges of 4.52~50.00°. No significant decay was observed during the data collection. Data were processed on a Pentium PC using the Bruker AXS Crystal Structure Analysis Package, Version 5.10.

Example 10

Synthesis of Polystyrene in Nonionic DBU/1-propanol and Facile Collection in Ionic DBU/1-propanol DBU (3.0 mL) and 1-propanol (3.6 mL) (1:2.5 mol/mol) were placed in a 2-necked flask under an $N_2$ atmosphere. $K_2S_2O_8$ (50 mg) was added followed by 2.0 mL of distilled styrene. The flask was stirred with a condenser attached for 12 hours at 50° C. After the polymerization reaction forming polystyrene was complete, the solution appeared clear and yellow, and no precipitate was visible. $CO_2$ was bubbled through the solution for 1 hour to convert the solvent to its ionic form. 1-propanol (1.5 mL) was added to decrease the viscosity. Polystyrene precipitated out of the ionic liquid and was filtered in an air-free Schlenk filter under $N_2$. This completed the first cycle. The collected polystyrene was washed with cold MeOH and characterized.

To the recycled solvent, DBU (0.6 mL) and distilled styrene (1.0 mL) were added, followed by $K_2S_2O_8$ (25 mg). The reaction was allowed to proceed for 12 hours at 50° C. $CO_2$ was bubbled through the solution for 1 hour to convert the solvent to its ionic form and 1.5 mL of 1-propanol was added to decrease the viscosity. Polystyrene precipitated and was filtered and characterized. This completed the second cycle. The same method was repeated for third and fourth cycles (i.e., each time adding propanol, then adding the corresponding DBU quantity, to restore their initial molar ratio). The solvent was yellow for each cycle after the first.

Information regarding switchable solvents appears in Jessop, P. G.; Heldebrant, D. J.; Li, X.; Eckert, C. A.; Liotta, C. L. "A Reversible Ionic/Non-Ionic Switchable Solvent," *Nature* 436, 1102 (2005), which is hereby incorporated in its entirety by reference. Furthermore, all scientific and patent publications cited herein are hereby incorporated in their entirety by reference.

It will be understood by those skilled in the art that this description is made with reference to the preferred embodiments and that it is possible to make other embodiments employing the principles of the invention which fall within its spirit and scope as defined by the claims appended hereto.

REFERENCES

Aki, S, N. V. K.; Brennecke, J. F.; Samanta, A., "How polar are room-temperature ionic liquids?" *Chem. Commun.* 413-414 (2001).

Carmichael, A. J. & Seddon, K. R. "Polarity study of some 1-alkyl-3-methylimidazolium ambient-temperature ionic liquids with the solvatochromic dye, Nile Red." *J. Phys. Org. Chem.* 13, 591-595 (2000).

Cost, M.; Chiusoli, G. P.; Taffurelli D.; Dalmonego, G.; "Superbase catalysis of oxazolidin-2-one ring formation from carbon dioxide and prop-2-yn-1-amines under homogeneous or heterogeneous conditions." *J. Chem. Soc., Perkin Trans.* 1, (1998) 9:1541-1546.

Deye, J. F.; Berger, T. A.; Anderson, A. G. "Nile Red as solvatochromic dye for measuring solvent strength in normal liquids and mixtures of normal liquids with supercritical fluids and near critical fluids." *Anal. Chem.* 62, 615-622 (1990).

Jessop, P. G.; Leitner, W., *Chemical Synthesis using Supercritical Fluids.* VCH/Wiley: Weinheim, Germany (1999).

Jen, W. S.; Wiener, J. J. M.; MacMillan, D. W. C. "New strategies for organic catalysis: The first enantioselective organocatalytic 1,3-dipolar cycloaddition" *J. Am. Chem. Soc.* (2000) 122(40): 9874-9875.

Jessop, P. G.; Heldebrant, D. J.; Li, X.; Eckert, C. A.; Liotta, C. L. "A reversible ionic/non-ionic switchable solvent," *Nature* 436, 1102 (2005).

Hori, Y.; Nagano, Y.; Nakau, J.; Taniguchi, H. "New method of organic synthesis using DBU (6th report) Reversible Immobilization of Carbon Dioxide Gas by Forming Carbonate, Carbamate Salt." Kinki Chemical Society, Japan, *Chemistry Express* 1(3): 173-176 (1986).

Main, A. D.; Fryxell, G. E.; Linehan, J., "Simple preparation of organic salts of alkyl carbonates: an alternate synthesis of dimethyl carbonate", unpublished material (2001).

Muldoon, M. J., Gordon, C. M. & Dunkin, I. R. "Investigations of solvent-solute interactions in room temperature ionic liquids using solvatochromic dyes." *J. Chem. Soc.-Perkin Trans. 2*, 433-435 (2001).

Munshi, P.; Main, A. D.; Linehan, J.; Tai, C. C.; Jessop, P. G., "Hydrogenation of carbon dioxide catalysed by ruthenium trimethylphosphine complexes: the accelerating effect of certain alcohols and amines." *J. Am. Chem. Soc.* 124, 7963-7971 (2002).

Perez, E. R.; Santos, R. H. A.; Gambardella, M. T. P.; de Macedo, L. G. M.; Rodrigues-Filho, U. P.; Launay, J.-C.; Franco, D. W., "Activation of carbon dioxide by bicyclic amidines". *J. Org. Chem.* 69, 8005-8011 (2004).

Reichardt, C. "Solvatochromic dyes as solvent polarity indicators." *Chem. Rev.* 94, 2319-2358 (1994).

Reichardt, C. "Polarity of ionic liquids determined empirically by means of solvatochromic pyridinium N-phenolate betaine dyes," *Green Chem.* 7, 339-351 (2005).

Reynders, P., Kuehnle, W. & Zachariasse, K. A. "Ground-state dimers in excimer-forming bichromophoric molecules. 1. Bis(pyrenylcarboxy)alkanes." *J. Am. Chem. Soc.* 112, 3929-3939 (1990).

Sakai, S., Kobayashi, Y. & Isii, Y. "Reaction of dialkyltin dialkoxides with carbon disulfide at higher temperature. Preparation of orthocarbonates." *J. Org. Chem.* 36, 1176-1180 (1971).

Subramaniam, B.; Busch, D. H., "Use of dense-phase carbon dioxide in catalysis", *Carbon Dioxide Conversion and Utilization*, Song, C.; Gaffney, A. F.; Fujimoto, K., Eds. ACS: Washington, pp 364-386 (2002).

Schuchardt, U.; Vargas R. M.; Gelbard, G.; "Alkylguanidines as catalysts for the transesterification of rapeseed oil" *J. Mol. Cat A: Chem*, 99: 65 (1995).

Verdecchia, M., Feroci, M., Palombi, L. & Rossi, L. "A safe and mild synthesis of organic carbonates from alkyl halides and tetrabutylammonium alkyl carbonates." *J. Org. Chem.* 67, 8287-8289 (2002).

Yamada, T.; Lukac, P. J.; George, M.; Weiss, R. G. "Reversible, room-temperature ionic liquids, amidinium carbamates derived from amidines and aliphatic primary amines with carbon dioxide." *Chem. Mater.* 19: 967-969 (2007).

TABLE 1

Miscibility of the [DBUH][O$_2$COR] ionic liquids with hexane, toluene and ethyl acetate (traditional nonpolar solvents)

| R of [O$_2$COR] | Miscible with Hexanes? | Miscible with Toluene? | Miscible with Ethyl acetate? |
|---|---|---|---|
| Ethyl | No | No | No |
| 1-Butyl | No | Yes | Yes |
| 1-Hexyl | No | Yes | Yes |
| 1-Octyl | No | Yes | Yes |
| 1-Decyl | Yes | Yes | Yes |

TABLE 2

$^{13}$C{$^1$H} NMR chemical shifts of [DBUH][O$_2$COR] salts in CDCl$_3$

| | | | R of [$^-$O$_2$COR] | | | |
|---|---|---|---|---|---|---|
| Carbon | H | ethyl | 1-propyl | 1-butyl | 1-hexyl | 1-octyl | 1-decyl |
| [O$_2$COR] | 161.1 | 158.6 | 158.6 | 157.8 | 158.7 | 157.5 | 158.3 |
| DBU C$_2$ | 53.2 | 53.5 | 53.9 | 52.9 | 53.5 | 52.6 | 53.3 |
| DBU C$_3$ | 29.7 | 27.1 | 26.9 | 28.1 | 26.8 | 26.7 | 26.4 |
| DBU C$_4$ | 28.3 | 28.9 | 28.9 | 23.5 | 28.8 | 23.3 | 23.7 |
| DBU C$_5$ | 25.7 | 24.4 | 25.9 | 26.2 | 24.0 | 28.0 | 28.6 |
| DBU C$_6$ | 36.6 | 33.1 | 31.5 | 31.0 | 32.3 | 31.8 | 31.7 |
| DBU C$_7$ | 162.6 | 164.4 | 164.9 | 164.2 | 164.9 | 163.6 | 164.8 |
| DBU C$_9$ | 43.1 | 39.4 | 38.4 | 38.1 | 38.6 | 38.2 | 38.0 |
| DBU C$_{10}$ | 22.0 | 20.1 | 19.5 | 19.1 | 19.7 | 19.0 | 19.2 |
| DBU C$_{11}$ | 48.5 | 48.2 | 48.5 | 47.5 | 48.1 | 47.2 | 47.8 |
| ROH C$_1$ | na | 60.0 | 65.7 | 63.5 | 64.6 | 63.5 | 64.2 |
| ROH C$_2$ | na | 15.1 | 31.5 | 31.7 | 29.4 | 28.6 | 28.6 |
| ROH C$_3$ | na | na | 19.1 | 18.3 | 25.5 | 25.0 | 25.3 |
| ROH C$_4$ | na | na | na | 13.0 | 31.5 | 28.0 | 29.0 |
| ROH C$_5$ | na | na | na | na | 22.2 | 28.0 | 29.0 |
| ROH C$_6$ | na | na | na | na | 13.7 | 30.5 | 29.0 |
| ROH C$_7$ | na | na | na | na | na | 21.3 | 29.0 |
| ROH C$_8$ | na | na | na | na | na | 12.8 | 31.1 |
| ROH C$_9$ | na | na | na | na | na | na | 21.9 |
| ROH C$_{10}$ | na | na | na | na | na | na | 13.4 | na = not applicable

TABLE 3

$^{13}$C{$^1$H} NMR chemical shifts of pure n-alcohols in CDCl$_3$

| Carbon | Ethanol | Propanol | Butanol | Hexanol | Octanol | Decanol |
|---|---|---|---|---|---|---|
| ROH C1 | 58.0 | 64.5 | 62.4 | 62.7 | 62.9 | 62.9 |
| ROH C2 | 18.3 | 26.0 | 34.8 | 32.7 | 32.9 | 32.8 |
| ROH C3 | na | 10.2 | 19.0 | 25.4 | 25.8 | 25.9 |
| ROH C4 | na | na | 13.9 | 31.6 | 29.3 | 29.6 |
| ROH C5 | na | na | na | 22.5 | 29.4 | 29.6 |
| ROH C6 | na | na | na | 14.0 | 31.8 | 29.6 |
| ROH C7 | na | na | na | na | 22.7 | 29.4 |
| ROH C8 | na | na | na | na | 14.1 | 32.0 |
| ROH C9 | na | na | na | na | na | 22.8 |
| ROH C10 | na | na | na | na | na | 14.2 | na = not applicable

TABLE 4

$^1$H NMR chemical shifts of [DBUH][O$_2$COR] salts in CDCl$_3$

| | R of [$^-$O$_2$COR] | | | | | |
|---|---|---|---|---|---|---|
| Proton position | H | Ethyl | 1-butyl | 1-hexyl | 1-octyl | 1-decyl |
| DBU C2 | 3.39 | 3.61 | 3.54 | 3.49 | 3.53 | 3.53 |
| DBU C3 | 1.72 | 1.74 | 1.73 | 1.75 | 1.70 | 1.76 |

TABLE 4-continued $^1$H NMR chemical shifts of [DBUH][O$_2$COR] salts in CDCl$_3$

| Proton position | R of [$^-$O$_2$COR] | | | | | |
|---|---|---|---|---|---|---|
| | H | Ethyl | 1-butyl | 1-hexyl | 1-octyl | 1-decyl |
| DBU C4 | 1.65 | 1.74 | 1.73 | 1.75 | 1.60 | 1.76 |
| DBU C5 | 1.72 | 1.74 | 1.73 | 1.75 | 1.75 | 1.76 |
| DBU C6 | 2.71 | 2.86 | 2.79 | 2.81 | 2.77 | 2.84 |
| DBU C9 | 3.39 | 3.42 | 3.40 | 3.43 | 3.39 | 3.43 |
| DBU C10 | 1.94 | 2.05 | 2.01 | 2.00 | 2.00 | 2.02 |
| DBU C11 | 3.39 | 3.61 | 3.54 | 3.49 | 3.53 | 3.53 |
| ROH C1 | na | 3.91 | 3.88 | 3.90 | 3.88 | 3.89 |
| ROH C2 | na | 1.19 | 1.6 | 1.58 | 1.58 | 1.59 |
| ROH C3 | na | na | 1.41 | 1.37 | 1.36 | 1.27 |
| ROH C4 | na | na | 0.92 | 1.29 | 1.28 | 1.27 |
| ROH C5 | na | na | na | 1.29 | 1.28 | 1.27 |
| ROH C6 | na | na | na | 0.87 | 1.28 | 1.27 |
| ROH C7 | na | na | na | na | 1.28 | 1.27 |
| ROH C8 | na | na | na | na | 0.88 | 1.27 |
| ROH C9 | na | na | na | na | na | 1.27 |
| ROH C10 | na | na | na | na | na | 0.88 | na = not applicable
Strongly overlapped peaks have been given identical chemical shifts.

TABLE 5

$^1$H NMR chemical shifts of pure n-alcohols in CDCl$_3$

| Proton Position | EtOH | PrOH | BuOH | Hexanol | Octanol | Decanol |
|---|---|---|---|---|---|---|
| ROH C1 | 3.68 | 3.58 | 3.62 | 3.63 | 3.62 | 3.61 |
| ROH C2 | 1.22 | 1.58 | 1.55 | 1.58 | 1.56 | 1.56 |
| ROH C3 | na | 0.93 | 1.38 | 1.30 | 1.30 | 1.27 |
| ROH C4 | na | na | 0.93 | 1.30 | 1.30 | 1.27 |
| ROH C5 | na | na | na | 1.30 | 1.30 | 1.27 |
| ROH C6 | na | na | na | 0.91 | 1.30 | 1.27 |
| ROH C7 | na | na | na | na | 1.30 | 1.27 |
| ROH C8 | na | na | na | na | 0.88 | 1.27 |
| ROH C9 | na | na | na | na | na | 1.31 |
| ROH C10 | na | na | na | na | na | 0.88 | na = not applicable

TABLE 6

$^1$H NMR chemical shifts for key protons observed in n-hexanol, DBU, and mixtures of n-hexanol and DBU

| Solvent | Pure hexanol or DBU in CDCl$_3$ | Nonionic Liquid | | Ionic Liquid | |
|---|---|---|---|---|---|
| | CDCl$_3$ | CDCl$_3$ | Neat | CDCl$_3$ | neat |
| Sample | pure | 1:1 mix$^a$ | 1:1 mix$^a$ | 1:1 mix$^a$ | 1:1 mix$^a$ |
| CO$_2$ | absent | absent | absent | present | present |
| Protons on C1 of hexanol$^b$ | 3.58 | 3.56 | 3.38 | 3.90 | 3.69 |
| Protons on CH$_3$ of hexanol$^b$ | 0.82 | 0.80 | 0.85 | 0.87 | 0.85 |
| Protons on C2, C9 and C11 of DBU$^b$ | 3.1-3.3 | 3.1-3.3 | 3.1-3.2 | 3.4-3.5 | 3.2-3.5 |
| Protons on C6 of DBU$^b$ | 2.38 | 2.37 | 2.28 | 2.81 | 2.75 |

$^a$1:1 mole ratio of DBU and 1-hexanol.
$^b$The internal methylene protons in hexanol (1.2 to 1.5 ppm) and methylenes on C3, C4, C5, and C10 of DBU at 1.5 to 1.8 ppm are heavily overlapped with other peaks in the spectra of the mixtures.

TABLE 7

$^1$H NMR spectroscopic data for amines and their carbamate salts in CDCl$_3$$^{a,b}$

| Species | C1 | C2 | C3 | C4 | C1' | C2' |
|---|---|---|---|---|---|---|
| NHBuEt | 2.55 t | 1.42 qn | 1.28 sx | 0.86 t | 2.59 q | 1.05 t |
| | 7.6 Hz | 7.5 Hz | 7.5 Hz | 7.4 Hz | 7.0 Hz | 7.2 Hz |
| NHBuEt | 3.15 br | 1.44 br | 1.26 br | 0.84 t | 3.15 br | 1.02 br |
| carbamate | 2.68 br | 1.98 br | | 7.4 Hz | 2.78 br | 1.18 br |
| [NH$_2$BuEt]Cl | 2.85 t | 1.82 qn | 1.36 sx | 0.88 t | 2.97 q | 1.42 t |
| | 7.8 Hz | 7.8 Hz | 7.6 Hz | 7.4 Hz | 6.8 Hz | 7.4 Hz |
| NHBuMe neutral | 2.50 t | 1.40 qn | 1.27 sx | 0.85 t | 2.36 s | — |
| | 7.0 Hz | 7.3 Hz | 7.2 Hz | 7.2 Hz | | |
| NHBuMe carbamate | 2.94 br | 1.32 br | 1.04 br | 0.62 t | 2.54 br | — |
| | 2.54 br | 1.20 br | | 7.4 Hz | 2.27 br | |
| NHBuMe•HCl | 2.95 t | 1.87 qn | 1.46 sx | 0.98 t | 2.70 s | — |
| | 7.8 Hz | 7.8 Hz | 7.5 Hz | 7.4 Hz | | |
| NHPr$_2$ | 2.49 t | 1.44 sx | 0.84 t | — | — | — |
| | 7.2 Hz | 7.2 Hz | 7.4 Hz | | | |
| NHPr$_2$ carbamate | 2.73 br | 1.70 br | 0.89 br | — | — | — |
| | 3.17 br | 1.54 br | | | | |
| NHPr$_2$•HCl | 2.91 br | 1.96 sx | 1.03 t | — | — | — |
| | | 7.9 Hz | 7.4 Hz | | | |
| NHMeBz | 3.68 s | 7.1-7.3 | — | — | 2.39 s | — |
| NHMeBz carbamate | 4.43 | 7.1-7.4 | — | — | 2.80 s | — |
| | 3.78 s | | | | 2.27 s | |
| NHMeBz•HCl | 3.96 s | 7.4-7.6 | — | — | 2.42 s | — |

$^a$Abbreviations: br = broad, s = singlet, d = doublet, t = triplet, q = quartet, qn = quintet or apparent quintet, sx = sextet or apparent sextet.
$^b$C1-C4 refers to the longer chain of the two substituents (e.g., Bu), C1'-C2' refers to the shorter of the two substituents (e.g., Et).

TABLE 8

$^{13}$C NMR spectroscopic data for amines and their carbamate and HCl salts in CDCl$_3$, with all chemical shifts relative to CDCl$_3$ at 77.0 ppm$^a$

| Species | C1 | C2 | C3 | C4 | C1' | C2' | CO |
|---|---|---|---|---|---|---|---|
| NHBuEt | 49.4 | 32.1 | 20.4 | 13.9 | 44.0 | 15.1 | — |
| NHBuEt carbamate | 46.6 | 30.6 | 19.8 | 13.4 | 41.8 | 11.6 | 161.5 |
| | 45.7 | 28.5 | | | 40.8 | | |
| NHBuEt•HCl | 47.1 | 27.9 | 20.1 | 13.5 | 42.7 | 11.1 | — |
| NHBuMe | 51.9 | 32.1 | 20.4 | 14.0 | 36.5 | — | — |
| NHBuMe carbamate | 48.1 | 29.6 | 19.5 | 13.2 | 33.4 | — | 161.9 |
| | | 27.6 | | | 32.3 | | |
| NHBuMe•HCl | 49.2 | 27.8 | 20.0 | 13.5 | 32.8 | — | — |
| NHPr$_2$ | 51.9 | 23.2 | 11.7 | — | — | — | — |
| NHPr$_2$ carbamate | 48.9 | 21.2 | 10.8 | — | — | — | 161.2 |
| | 48.1 | 19.7 | | | | | |
| NHPr$_2$•HCl | 49.3 | 19.4 | 11.3 | — | — | — | — |
| NHMeBz | 56.1 | 140.4 | — | — | 36.1 | — | — |
| | | 128.4 | | | | | |
| | | 128.1 | | | | | |
| | | 126.9 | | | | | |
| NHMeBz carbamate | 51.8 | 138.8 | — | — | 33.5 | — | 161.7 |
| | 39.8 | 132.6 | | | 31.0 | | |
| | | 125-132 | | | | | |
| NHMeBz•HCl | 52.1 | 130.3 | — | — | 31.2 | — | — |
| | | 129.8 | | | | | |
| | | 129.6 | | | | | |
| | | 129.2 | | | | | |

$^a$C1-C4 refers to the longer chain of the two substituents (e.g., Bu), C1'-C2' refers to the shorter of the two substituents (e.g., Et).

TABLE 9

IR spectroscopic data for the carbamate salts of selected secondary amines

| Amine | IR bands detected | | | | | | | | | | |
|---|---|---|---|---|---|---|---|---|---|---|---|
| Dipropyl | 1618 | 1459 | 1259 | 1093 | 1017 | 2955 | 2927 | 2869 | 1376 | | |
| SecButylpropyl | 1679 | 1647 | 1466 | 1408 | 1170 | 1065 | 2331 | 2360 | 2927 | 2869 | 2959 |
| Ethylbutyl | 1618 | 1539 | 1472 | 1408 | 1370 | 1300 | 1065 | 2335 | 2357 | 2869 | 2927 | 2962 |
| Methylbenzyl | 1622 | 3029 | 2844 | 2790 | 1545 | 1491 | 1450 | 1380 | 1262 | 1023 | |
| Methylbutyl | 1626 | 2962 | 2859 | 1545 | 1471 | 1382 | 1305 | 932 | 810 | 1057 | |

TABLE 10

Comparison of polarities of ethylbutylamine and DBU/1-hexanol in ionic and nonionic forms to polarities of traditional solvents[a]

| Solvent | $\lambda_{max}$ (Nile Red), nm |
|---|---|
| Methanol | 550 |
| DBU + hexanol + $CO_2$ | 545 |
| Propanoic acid | 542 |
| DMF | 541 |
| $CHCl_3$ | 538 |
| DBU + hexanol − $CO_2$ | 538 |
| $CH_2Cl_2$ | 535 |
| EtBuNH + $CO_2$ | 531 |
| THF | 528 |
| toluene | 522 |
| EtBuNH − $CO_2$ | 517 |
| Ether | 504 |

[a]+$CO_2$ indicates ionic form; −$CO_2$ indicates nonionic form

TABLE 11

Qualitative study of viscosity of secondary amines in the presence and absence of $CO_2$

| Compound | Effect of $CO_2$ on viscosity | Effect of $N_2$ on viscosity |
|---|---|---|
| N-propyl-sec-butylamine | Increase | Decrease |
| N-propylbutylamine | Increase | Decrease |
| N-ethylbutylamine | Increase | Decrease |
| Dipropylamine | Increase | Decrease |
| N-methylbutylamine | Increase | Decrease |
| N-methylpropylamine | Increase | Decrease |
| N-methylpentylamine | Increase | Decrease |
| N-benzylmethylamine | Increase | Decrease |
| Methylaniline | No change | No change |
| Ethylene diamine | Very strong increase | — |
| 1,3-dimethylbutylamine | Solidified | — |
| Hexylamine | Solidified | — |
| N-tert-butyl-isopropylamine | Solidified | — |

TABLE 12

Wavelengths of secondary amines in the presence and absence of $CO_2$

| Compound | $\lambda_{max}$ non-ionic form (nm) | $\lambda_{max}$ ionic form (nm) | $\lambda_{max}$ (reformed) non-ionic form (nm) |
|---|---|---|---|
| N-propyl-sec-butylamine | 504 | 519 | 500 |
| N-propylbutylamine | 516 | 523 | 516 |
| N-Ethylbutylamine | 517 | 531 | 517 |
| Dipropylamine | 518 | 531 | 521 |
| N-methylbutylamine | 519 | 536 | 530* |
| N-methylpropylamine | 525 | 537 | 536* |
| N-benzylmethylamine | 534 | 543 | 536 |
| Methylaniline | Shoulder at 475, no shift | | |

*Remained constant after 2.5 hours under rapid nitrogen at 60° C.

TABLE 13

Miscibility of selected liquids in NHEtBu and its carbamate salt.

| Solute | Non-ionic form | Ionic form |
|---|---|---|
| Decane | Y | Y |
| Trans-5-decene | Y | Y |
| Hexadecane | Y | Y |
| Toluene | Y | Y |
| Mesitylene | Y | Y |
| Styrene | Y | Y |
| Propylene carbonate | Y | Y |
| Water | Y | Y |

TABLE 14

Solubility of selected solutes in NHEtBu and in its carbamate salt

| Solute | NHEtBu | [$NH_2$EtBu][$O_2$CNEtBu] |
|---|---|---|
| tetracosane $C_{24}H_{50}$ | Y | N |
| polystyrene MW 100K crushed | Y | N |
| polystyrene MW 2K | Y | N |
| benzyl benzamide | Y | Y |
| stilbene | Y | N |
| poly(sodium-4-styrene sulfonate) | Y | Y |
| poly(acrylic acid) sodium salt | Y | Y |
| tetraethylammonium p-toluenesulfonate | N | Y |
| sodium toluenesulfonate | N | Y |
| benzyltriethylammonium chloride | N | N |
| cellulose | N | N |
| glucose | N | Y |
| (vinylbenzyl)trimethylammonium chloride | N | N |

Conditions: 50 mg solute in 2.22 mL of NHEtBu or its carbamate form

TABLE 15

Solubility of selected solutes in DBU/1-propanol mixture and in its alkylcarbonate salt

| Solute | Non-ionic form | Ionic form |
| --- | --- | --- |
| Decane | Y | N |
| Polystyrene | Y | N |
| Toluene | Y | Y |
| [PhCH$_2$NEt$_3$]Cl | N | Y |
| Glucose | N | N |
| [NEt$_4$][O$_3$SC$_6$H$_4$Me] | N | N |

Conditions: 50 mg solid solute in 2.22 mL of solvent; or 0.5 mL of liquid solute in 2.22 mL of solvent.

We claim:

1. A composition comprising:
(a) CO$_2$ from a source other than air; and
(b) a switchable solvent from by combining:
an amount of at least one R'OH, water, or a combination thereof, wherein R' is alkyl, alkenyl, alkynyl, aryl, silyl, or siloxyl, and may be linear, branched, or cyclic, and may be substituted or unsubstituted;
with an amount of a compound of formula (3)

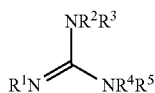

(3)

wherein
R$^1$, R$^2$, R$^3$, R$^4$, and R$^5$ are independently H; a substituted or unsubstituted C$_1$ to C$_{10}$ alkyl group that is linear or branched; a substituted or unsubstituted C$_3$ to C$_{10}$ cycloalkyl group; a substituted or unsubstituted C$_n$Si$_m$ group where n and m are independently a number from 0 to 10 and n+m is a number from 1 to 10; a substituted or unsubstituted aryl group optionally containing one or more {—Si(R$^6$)$_2$—O—} units; or a substituted or unsubstituted heteroaryl group optionally containing one or more {—Si(R$^6$)$_2$—O—} units; R$^6$ is a substituted or unsubstituted alkyl, aryl, heteroaryl, or alkoxy moiety; and wherein the compound of formula (3) and the corresponding ionic liquid of formula (4) may be a monocyclic or bicyclic ring structure;
wherein the compound of formula (3) reversibly converts to an ionic liquid of formula (4)

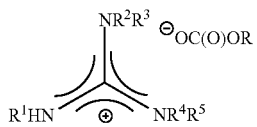

(4)

in the presence of the CO$_2$, wherein R is H or R' as defined above, and R$^1$, R$^2$, R$^3$, R$^4$, and R$^5$ are as defined above; and
wherein the amount of the compound of formula (3) is approximately equimolar to or greater than equimolar to the amount of the at least one R'OH, water, or combination thereof.

2. The composition of claim 1, wherein the CO$_2$ is gaseous and is present at a pressure of at least 1 atm.

3. The composition of claim 1, wherein the CO$_2$ is gaseous and is present at a pressure of greater than 1 atm.

4. The composition of claim 1, wherein R$^1$, R$^2$, R$^3$, R$^4$, and R$^5$ are not hydrogen.

5. The composition of claim 1, wherein the compound of formula (3) is a monocyclic or bicyclic ring structure.

6. The composition of claim 5, wherein the compound of formula (3) is 1,3,4,6,7,8-hexahydro-1-methyl-2H-pyrimido[1,2-a]pyrimidine ("MeMTBD").

7. The composition of claim 1, wherein the ionic liquid of formula (4) is a monocyclic or bicyclic ring structure.

8. The composition of claim 7, wherein the ionic liquid of formula (4) is protonated 1,3,4,6,7,8-hexahydro-1-methyl-2H-pyrimido[1,2-a]pyrimidine ("MeMTBDH$^+$")HOCO$_2^-$.

9. The composition of claim 1, wherein the at least one R'OH is a primary or a secondary alcohol.

10. The composition of claim 1, wherein one or more of R$^1$, R$^2$, R$^3$, R$^4$, and R$^5$ is substituted with hydroxyl.

11. The composition of claim 1, wherein R' is substituted with one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

12. The composition of claim 1, wherein one or more of R$^1$, R$^2$, R$^3$, R$^4$, R$^5$, and R$^6$ is independently substituted with one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

13. The composition of claim 1, wherein the ionic liquid is [MeMTBDH]$^+$[ROCO$_2$]$^-$ where R is R' and the at least one R'OH comprises 1-propanol, 1-butanol, 1-hexanol, 1-octanol, 2-octanol, 1-decanol, or phenol.

14. The composition of claim 1, wherein the amount of the compound of formula (3) is approximately equimolar to the amount of the at least one R'OH, water or combination thereof.

15. The composition of claim 1, wherein the amount of the compound of formula (3) is greater than equimolar to the amount of the at least one R'OH, water or combination thereof.

16. The composition of claim 1, wherein R$^1$, R$^2$, R$^3$, R$^4$, and R$^5$ are independently a substituted or unsubstituted C$_1$ to C$_4$ alkyl group that is linear or branched.

17. The composition of claim 1, wherein R is H or alkyl.

18. A composition comprising:
(a) CO$_2$ from a source other than air; and
(b) a switchable solvent formed by combining:
at least one R'OH, water, or a combination thereof, wherein R' is alkyl, alkenyl, alkynyl, aryl, silyl, or siloxyl, and may be linear, branched, or cyclic, and may be substituted or unsubstituted;
with a compound of formula (3)

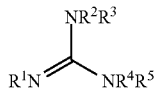

(3)

wherein
$R^1$, $R^2$, $R^3$, $R^4$, and $R^5$ are independently H; a substituted or unsubstituted $C_1$ to $C_4$ alkyl group that is linear or branched; a substituted or unsubstituted $C_nSi_m$ group where n and m are independently a number from 0 to 4 and n+m is a number from 1 to 4; a substituted or unsubstituted $C_3$ to $C_4$ cycloalkyl group; a substituted or unsubstituted heteroaryl group optionally containing one or more {—Si($R^6$)$_2$—O—} units; $R^6$ is a substituted or unsubstituted alkyl, aryl, heteroaryl, or alkoxy moiety; and wherein the compound of formula (3) and the corresponding ionic liquid of formula (4) may be a monocyclic or bicyclic ring structure;
wherein the compound of formula (3) reversibly converts to an ionic liquid of formula (4)

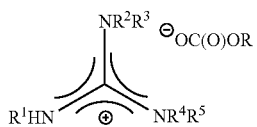

(4)

in the presence of the $CO_2$, wherein R is H or R' as defined above, and $R^1$, $R^2$, $R^3$, $R^4$, and $R^5$ are as defined above.

19. The composition of claim 18, wherein the $CO_2$ is gaseous and is present at a pressure of at least 1 atm.

20. The composition of claim 18, wherein the $CO_2$ is gaseous and is present at a pressure of greater than 1 atm.

21. The composition of claim 18, wherein $R^1$, $R^2$, $R^3$, $R^4$, and $R^5$ are not hydrogen.

22. The composition of claim 18, wherein the compound of formula (3) is a monocyclic or bicyclic ring structure.

23. The composition of claim 22, wherein the compound of formula (3) is 1,3,4,6,7,8-hexahydro-1-methyl-2H-pyrimido[1,2-a]pyrimidine ("MeMTBD").

24. The composition of claim 18, wherein the ionic liquid of formula (4) is a monocyclic or bicyclic ring structure.

25. The composition of claim 24, wherein the ionic liquid of formula (4) is protonated 1,3,4,6,7,8-hexahydro-1-methyl-2H-pyrimido[1,2-a]pyrimidine ("MeMTBDH$^+$")HOCO$_2^-$.

26. The composition of claim 18, wherein the at least one R'OH is a primary or a secondary alcohol.

27. The composition of claim 18, wherein R' is substituted with one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

28. The composition of claim 18, wherein one or more of $R^1$, $R^2$, $R^3$, $R^4$, $R^5$, and $R^6$ is independently substituted with one or more of heteroaryl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, thioester, and alkyl halide; and
substituents for $R^6$ include one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

29. The composition of claim 28, wherein one or more of $R^1$, $R^2$, $R^3$, $R^4$, and $R^5$ is substituted with hydroxyl.

30. The composition of claim 18, wherein the ionic liquid is [MeMTBDH]$^+$[ROCO$_2$]$^-$ where R is R' and the at least one R'OH comprises 1-propanol, 1-butanol, 1-hexanol, 1-octanol, 2-octanol, 1-decanol, or phenol.

31. The composition of claim 18, wherein the compound of formula (3) and the at least one R'OH, water or combination thereof are present in approximately equimolar amounts.

32. The composition of claim 18, wherein the compound of formula (3) is present at an amount that is less than equimolar to the amount present of the at least one R'OH, water or combination thereof.

33. The composition of claim 18, wherein the compound of formula (3) is present at an amount that is more than equimolar to the amount present of the at least one R'OH, water or combination thereof.

34. The composition of claim 18, wherein $R^1$, $R^2$, $R^3$, $R^4$, and $R^5$ are independently an unsubstituted $C_1$ to $C_4$ alkyl group that is linear or branched.

35. The composition of claim 18, wherein R is H or alkyl.

36. A composition comprising:
(a) $CO_2$ from a source other than air; and
(b) a switchable solvent having switchable polarity between a polar form and a nonpolar form, wherein said switchable solvent comprises:
at least one R'OH, water, or a combination thereof, wherein R' is alkyl, alkenyl, alkynyl, aryl, silyl, or siloxyl, and may be linear, branched, or cyclic, and may be substituted or unsubstituted; and a compound of formula (3)

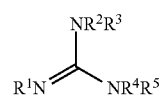

(3)

wherein
$R^1$, $R^2$, $R^3$, $R^4$, and $R^5$ are independently H; a substituted or unsubstituted $C_1$ to $C_{10}$ alkyl group that is linear or branched; a substituted or unsubstituted $C_3$ to $C_{10}$ cycloalkyl group; a substituted or unsubstituted $C_nSi_m$ group where n and m are independently a number from 0 to 10 and n+m is a number from 1 to 10; a substituted or unsubstituted aryl group optionally containing one or more {—Si(R$^6$)$_2$—O—} units; or a substituted or unsubstituted heteroaryl group optionally containing one or more {—Si(R$^6$)$_2$—O—} units; R$^6$ is a substituted or unsubstituted alkyl, aryl, heteroaryl, or alkoxy moiety; and wherein the compound of formula (3) and the corresponding ionic liquid of formula (4) may be a monocyclic or bicyclic ring structure; and wherein, optionally, one of R$^1$, R$^2$, R$^3$, R$^4$, and R$^5$ combines with R' to connect the hydroxyl of the at least one R'OH as part of the compound for formula (3);

wherein the compound of formula (3) reversibly converts to an ionic liquid of formula (4)

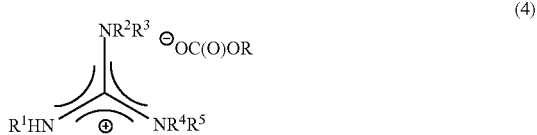

(4)

in the presence of the CO$_2$, wherein R is H or R' as defined above, and R$^1$, R$^2$, R$^3$, R$^4$, and R$^5$ are as defined above, wherein the polarity of the switchable solvent is switched by the interconversion of the compound of formula (3) and the ionic liquid of formula (4).

37. The composition of claim 36, wherein the CO$_2$ is gaseous and is present at a pressure of at least 1 atm.

38. The composition of claim 36, wherein the CO$_2$ is gaseous and is present at a pressure of greater than 1 atm.

39. The composition of claim 36, wherein R$^1$, R$^2$, R$^3$, R$^4$, and R$^5$ are not hydrogen.

40. The composition of claim 36, wherein the compound of formula (3) is a monocyclic or bicyclic ring structure.

41. The composition of claim 40, wherein the compound of formula (3) is 1,3,4,6,7,8-hexahydro-1-methyl-2H-pyrimido[1,2-a]pyrimidine ("MeMTBD").

42. The composition of claim 36, wherein the ionic liquid of formula (4) is a monocyclic or bicyclic ring structure.

43. The composition of claim 42, wherein the ionic liquid of formula (4) is protonated 1,3,4,6,7,8-hexahydro-1-methyl-2H-pyrimido[1,2-a]pyrimidine ("MeMTBDH$^+$")HOCO$_2^-$.

44. The composition of claim 36, wherein the at least one R'OH is a primary or a secondary alcohol.

45. The composition of claim 36, wherein R' is substituted with one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

46. The composition of claim 36, wherein one or more of R$^1$, R$^2$, R$^3$, R$^4$, and R$^5$ is independently substituted with one or more of alkyl, alkenyl, alkynyl, aryl, aryl halide, heteroaryl, cyclyl, Si(alkyl)$_3$, Si(alkoxy)$_3$, halo, alkoxyl, amino, amide, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, and alkyl halide.

47. The composition of claim 46, wherein one of R$^1$, R$^2$, R$^3$, R$^4$, and R$^5$ combines with R' to connect the hydroxyl of the at least one R'OH as part of the compound for formula (3).

48. The composition of claim 36, wherein the ionic liquid is [MeMTBDH]$^+$[ROCO$_2$]$^-$ where R is R' and the at least one R'OH comprises 1-propanol, 1-butanol, 1-hexanol, 1-octanol, 2-octanol, 1-decanol, or phenol.

49. The composition of claim 36, wherein the compound of formula (3) and the at least one R'OH, water or combination thereof are present in approximately equimolar amounts.

50. The composition of claim 36, wherein the compound of formula (3) is present at an amount that is less than equimolar to the amount present of the at least one R'OH, water or combination thereof.

51. The composition of claim 36, wherein the compound of formula (3) is present at an amount that is more than equimolar to the amount present of the at least one R'OH, water or combination thereof.

52. The composition of claim 36, wherein R$^1$, R$^2$, R$^3$, R$^4$, and R$^5$ are independently a substituted or unsubstituted C$_1$ to C$_4$ alkyl group that is linear or branched.

53. The composition of claim 36, wherein R is H or alkyl.

* * * * *